(12) United States Patent
Ohki et al.

(10) Patent No.: US 6,298,846 B1
(45) Date of Patent: Oct. 9, 2001

(54) SUCTION TYPE MEDICATOR

(75) Inventors: Hisatomo Ohki; Kazunori Ishizeki; Shigemi Nakamura; Yoshiyuki Yazawa, all of Gunma; Akira Yanagawa, Yokohama, all of (JP)

(73) Assignees: Unisia Jecs Corporation, Atsugi (JP); Dott Limited Company, Yokohama (JP)

(*) Notice: Subject to any disclaimer, the term of this patent is extended or adjusted under 35 U.S.C. 154(b) by 0 days.

(21) Appl. No.: 09/155,248

(22) PCT Filed: Jan. 29, 1998

(86) PCT No.: PCT/JP98/00360

§ 371 Date: Sep. 24, 1998

§ 102(e) Date: Sep. 24, 1998

(87) PCT Pub. No.: WO98/33540

PCT Pub. Date: Aug. 6, 1998

(30) Foreign Application Priority Data

Jan. 30, 1997 (JP) .................................................. 9-031121
Feb. 12, 1997 (JP) .................................................. 9-042897

(51) Int. Cl.[7] .................................................. A61M 15/00
(52) U.S. Cl. .............................. 128/203.15; 128/203.21; 604/58
(58) Field of Search .................. 128/203.15, 203.12, 128/203.21, 200.24; 604/58

(56) References Cited

U.S. PATENT DOCUMENTS

| | | | |
|---|---|---|---|
| 3,518,992 | * 7/1970 | Altounyan et al. | 128/203.15 |
| 4,889,114 | * 12/1989 | Kladders | 128/203.15 |
| 4,995,385 | * 2/1991 | Valentini et al. | 128/203.21 |
| 5,048,514 | * 9/1991 | Ramella | 128/203.21 |
| 5,152,284 | * 10/1992 | Valentini et al. | 128/203.21 |
| 5,568,807 | * 10/1996 | Mecikalski | 128/203.21 |
| 5,619,985 | 4/1997 | Ohki et al. | 128/203.21 |
| 5,647,349 | 7/1997 | Ohki et al. | 128/203.15 |
| 5,715,811 | 2/1998 | Ohki et al. | 128/203.21 |
| 5,752,505 | 5/1998 | Ohki et al. | 128/203.15 |
| 5,810,004 | 9/1998 | Ohki et al. | 128/203.15 |
| 5,899,202 | 5/1999 | Ohki et al. | 128/203.22 |
| 5,901,703 | 5/1999 | Ohki et al. | 128/203.12 |
| 5,921,236 | 7/1999 | Ohki et al. | 128/203.15 |
| 5,989,217 | 11/1999 | Ohki et al. | 604/94 |

* cited by examiner

Primary Examiner—Glenn K. Dawson
Assistant Examiner—Virendra K Srivastava
(74) Attorney, Agent, or Firm—Foley & Lardner

(57) ABSTRACT

A cylindrical main body 3 of a medicine administering device main body 1 is formed with a holder accommodating section 5, in which a capsule holding section 9 of a capsule holder 8 is disposed to be able to get in and out of the holder accommodating section 5. Accordingly, the capsule can be installed in a capsule fitting depression 10 formed in the capsule holding section 9, or the capsule after use can be taken out at a drawn-out position where the capsule holding section is drawn out of the holder accommodating section 5, so that installation and taking-out operations for the capsule can be easily made without decomposing respective parts like in a conventional technique. Additionally, the capsule can be located at a pushed-in position by pushing the capsule holding section 9 in the holder accommodating section 5.

Further, a burr releasing space is formed in a pin insertion hole located on an opposite side with respect to a perforating tool 25 so as to allow burr to be bent when a hole H1 is formed in the capsule K by a pin 27 of the perforating tool 25, thereby facilitating cleaning operation for removing broken pieces of the capsule K.

13 Claims, 18 Drawing Sheets

SUCTION TYPE MEDICATOR

FIELD OF THE INVENTION

This invention relates to an inhaling type medicine administering device, for example, suitable to be used for administering granular medicine into lungs under breathing-in action of a patient.

BACKGROUND TECHNIQUE

In general, as methods for administering medicine to the lungs of an asthma patient or the like, there are a method of injecting liquid medicine, a method of inhaling medicine by using a liquid aerosol sprayer, a method of inhaling fine granular medicine (having a grain size, for example, 5 to 10 $\mu$m) filled in a capsule.

Of these medicine administering methods for the asthma patient, the method of inhaling granular medicine filled in a capsule uses an inhaler which generally includes a body serving as a main body, a suction mouth which is detachably installed to the body and held in the mouth of the patient, a capsule holder which is disposed inside the body and holds a capsule filled with medicine, and an air flow passage whose inflow-side is opened to atmospheric air and whose outflow-side is opened to the above-mentioned suction mouth. Additionally, this inhaler is provided with a perforating tool and the like for forming holes in the capsule held in the capsule holder which holes are in communication with the air flow passage. The capsule holder is formed with pin insertion holes through which the pins of the above-mentioned perforating tool are inserted.

In case of inhaling medicine by using this inhaler, first the suction mouth, the capsule holder and the like are removed, and then the capsule is installed to the capsule holder, as a preparation operation for administering medicine. Thereafter, the capsule holder, the suction mouth and the like are installed to the body, and then the pins of the perforating tool are moved toward the capsule through the pin insertion holes thereby forming holes in the capsule which holes are in communication with the air flow passage.

Next, in order to make a medicine administering operation, the suction mouth is held in a mouth of the patient, and the patient breathes in under this state. By this, medicine inside the capsule can be mixed in air passing through the air flow passage, and therefore the patient can inhale medicine together with air to his or her lungs through the suction mouth.

After completion of the medicine administering operation, the suction mouth, the capsule holder and the like are removed from the body thereby taking out the used capsule from the capsule holder.

By the way, with the above-mentioned conventional inhaling type medicine administering device, the suction mouth and the capsule holder must be taken out of the body whenever the capsule is installed in the capsule holder and whenever the used capsule is taken out. As a result, treatment of the medicine administering device is troublesome during medicine administration, and problematic because there is the fear that the removed parts are lost.

Further, the number of contacts of the patient to the suction mouth and the capsule holder is increased during installation and removal of the capsule, and therefore this is problematic because of being not desirable from a sanitary viewpoint.

There is the possibility of the patient having a coughing fit when the patient inhales medicine. In this case, medicine is unavoidably released outside under the influence of reversely flowing air through the suction mouth, and therefore there is a problem that a predetermined amount of medicine cannot be inhaled.

Additionally, in such a conventional inhaled type medicine administering device, in order to secure a flow passage area between the inside of the capsule and the pin insertion hole, a clearance between the pin insertion hole and the pin of the perforating tool is minimized thereby punching a hole in the capsule under the action of the pin insertion hole and the pin.

As a result, a punched capsule piece unavoidably enters the pin insertion hole, and therefore a cleaning operation for removing this capsule piece is necessary, which is problematic because of being troublesome in treatment.

Additionally, there is the possibility that the capsule piece separated from the capsule is sucked together with medicine by the patient. In this case, the patient unavoidably has a coughing fit upon sucking the capsule piece. This is problematic because medicine cannot be effectively inhaled into the lungs.

Furthermore, since the clearance between the pin insertion hole and the pin is minimized, there are problems in which it is necessary to raise machining precision of respective parts; machining cost for the respective parts are increased; assembly operationability during production is degraded; and production cost is increased.

DISCLOSURE OF THE INVENTION

This invention has been accomplished in view of the above-discussed various problems of the conventional technique. The main object of the present invention is to provide an inhaling type medicine administering device which is simplified in operation of installing a capsule and taking out the capsule after inhaling medicine, thereby improving operationability of the medicine administering device during treatment of the medicine administering device.

Additionally, another object of the present invention is to provide an inhaling type medicine administering device which prevents medicine from being released outside under the influence of reversely flowing air through a suction mouth thereby making it possible to administer a predetermined amount of medicine to the patient.

A further object of the present invention is to provide an inhaling type medicine administering device which can prevent burr produced upon perforation during perforation of a capsule from being separated thereby facilitating treatment of the medicine administering device, while assembly precision between a pin insertion hole and a pin of a perforating tool can be lowered thereby improving productivity of the medicine administering device.

An inhaling type medicine administering device of the present invention comprises: a medicine administering device main body including a bolder accommodating section located at an axial one side of the above-mentioned main body, and a suction mouth located at an axial other side of the above-mentioned main body; a capsule holder which is disposed to be able to axially get in and off of the holder accommodating section of the medicine administering device main body and formed with a capsule holding space between it and the medicine administering device main body, a capsule being to be held in the capsule holding space; an air flow passage having an inflow-side for establishing communication between the above-mentioned capsule holding space and atmospheric air, and an outflow-side for establishing communication between the above-mentioned capsule holding space and the above-mentioned suction mouth in order to supply medicine within the capsule held in the above-mentioned capsule holding space to the side of the above-mentioned suction mouth; and a perforating tool disposed in the above-mentioned medicine administering device main body in order to form a hole in the capsule held in the above-mentioned capsule holding space, the hole being in communication with the air flow passage.

As thus arranged, in case that medicine is inhaled, first the capsule holder is drawn out of the holder accommodating section of the medicine administering device main body, and then the capsule is installed in the capsule holder in this state, as a medicine administration preparation operation. By inserting this capsule holder into the capsule accommodating section, the capsule can be held in the capsule holding space. Additionally, by perforating the capsule with the perforating tool, communication is established between the inside of the capsule and the air flow passage.

Next, in case of carrying out a medicine administration operation, the patient holds the medicine administering device main body in his or her mouth and breathes in under this state. By this, air flows to the inflow-side of the air flow passage, in which this air flows into the capsule thereby spreading medicine within the capsule. Medicine within the capsule flows together with air from the outflow-side of the air flow passage to the side of the suction mouth, and is inhaled into the patient's lungs through the suction mouth.

After completion of the medicine administration operation, the capsule holder can be drawn out of the holder accommodating section of the medicine administering device main body, thereby taking the used capsule out of the capsule holder.

Additionally, by further drawing out the capsule holder and separating the capsule holder from the medicine administering device main body, the holder accommodating section and the capsule holder can be easily rinsed.

Further, the above-mentioned air flow passage may include an inflow-side air flow passage which is located at the axial one side of the above-mentioned medicine administering device main body so as to be in communication with the above-mentioned capsule holding space; and an outflow-side air flow passage which is located at the axial other side of the above-mentioned medicine administering device main body so as to be in communication with the above-mentioned capsule holding space.

Furthermore, the above-mentioned air flow passage may include an inflow-side air flow passage which is located at the axial one side of the above-mentioned capsule holder so as to be in communication with the above-mentioned capsule holding space; and an outflow-side air flow passage which is located at the axial other side of the above-mentioned capsule holder so as to be in communication with the above-mentioned capsule holding space.

Moreover, the above-mentioned capsule holding space may be defined by a capsule fitting groove formed in the above-mentioned holder accommodating section of the above-mentioned medicine administering device main body, and a capsule fitting depression formed in the above-mentioned capsule holder.

Additionally, the above-mentioned capsule holder may include a reverse-flow preventing valve which is adapted to allow air through the above-mentioned air flow passage toward the suction mouth and to prevent air from flowing in a reverse direction.

Accordingly, in case of accomplishing the medicine administration operation, the patient holds the medicine administering device main body in his or her mouth and breathes in under this state. At this time, the reverse-flow preventing valve is opened, and therefore air can be flown though the air flow passage to the side of the suction mouth, so that the patient can inhale medicine within the capsule through the suction mouth into his or her lungs.

In case that the patient has a coughing fit in a state of holding the suction mouth in his or her mouth so that air makes its reverse flow into the suction mouth, the reverse-flow preventing valve is closed to impede flow in a reverse direction, thereby preventing medicine inside the capsule from being released out under the influence of this reversely flowing air.

Further, the above-mentioned capsule holder includes a grasping section for getting the above-mentioned capsule holder in and out of the above-mentioned holder accommodating section. Accordingly, when the capsule holder gets in and out of the holder accommodating section of the medicine administering device main body, the capsule holder can be get in and out by grasping the grasping section, and therefore the patient can be prevented from contacting with the air flow passage and the like when the patient takes the capsule out after inhalation of medicine.

Furthermore, a locating engagement section is formed between the holder accommodating section of the above-mentioned medicine administering device main body and the above-mentioned capsule holder, the above-mentioned locating engagement section being adapted to locate the above-mentioned capsule holder at a pushed-in position where the capsule holder is pushed in the holder accommodating section or at a drawn-out position where the capsule holder is drawn out of the holder accommodating section. Accordingly, in case that the capsule holder in which the capsule is installed is pushed in the holder accommodating section in order to inhale medicine, the capsule holder is located at the pushed-in position upon engagement of the locating engagement section. Besides, in case that the capsule is installed in the capsule holder and in case that the capsule holder is drawn out of the holder accommodating section in order to take out the capsule after inhalation of medicine, the capsule holder is located at the drawn-out position upon engagement of the locating engagement section.

Further, according to the present invention, the above-mentioned capsule holder and the like are formed with pin insertion holes in which pins of the above-mentioned perforating tool pierce. At least the above-mentioned pin insertion hole located at the side of the above-mentioned suction mouth, of the respective pins insertion holes, has a burr releasing space which allows burr to be bent, the above-mentioned burr being produced upon perforation when a hole is formed in the capsule.

Accordingly, in case of perforating the capsule with the perforating tool, the capsule is fitted in the capsule holding space or the capsule accommodating hole, and thereafter the pins of the perforating tool are moved toward the capsule. Then, the pins of the perforating tool is plunged into the capsule from a radially outward side thereby forming holes in the capsule which holes are in communication with the pin insertion holes. Capsule pieces produced at this time are stored inside the capsule.

Furthermore, the pins of the perforating tool are plunged into the capsule in such a manner as to radially project from the inside of the capsule, thereby forming holes which are in communication with the pin insertion holes which are located at an opposite side with respect to the perforating tool. At this time, burr produced upon perforation is bent within the burr releasing space in a state of being integral with the capsule since the pin insertion hole has the burr releasing space. As a result, the burr produced upon perforation can be prevented from separating from the capsule.

Besides, the above-mentioned burr releasing space is formed only in the pin insertion hole located at the side of the suction mouth, of the respective pin insertion holes. Consequently, when holes in communication with the pin insertion holes located at the side of the suction mouth are formed in the capsule, burr produced upon perforation is bent within the burr releasing space in a state of being integral with the capsule since the burr releasing space is formed only in this pin insertion hole.

Further, each pin of the above-mentioned perforating tool has a tip end section which is formed as an inclined face having an acute angle in section. The above-mentioned burr releasing space is formed at the rear end side of the inclined face of the above-mentioned pin so as to connect with the above-mentioned pin insertion hole. Accordingly, in case of forming holes in the capsule with the pins of the perforating tool, first the tip end section of the inclined face formed in each pin is plunged into the capsule, in which burr is formed in the capsule along with movement of the pin. This burr can be stored to be bent in the burr releasing space formed in the pin insertion hole and located at the rear end section side of the inclined face, and therefore the hole in communication with the pin insertion hole can be formed in the capsule without separation of the burr from the capsule.

BRIEF DESCRIPTION OF DRAWINGS

FIG. 16 is an enlarged fragmentary sectional view of an essential part, showing a holder accommodating section, the capsule holder, pins of a perforating tool, and the like.

THE BEST MODE FOR CARRYING OUT THE INVENTION

Figure 1:
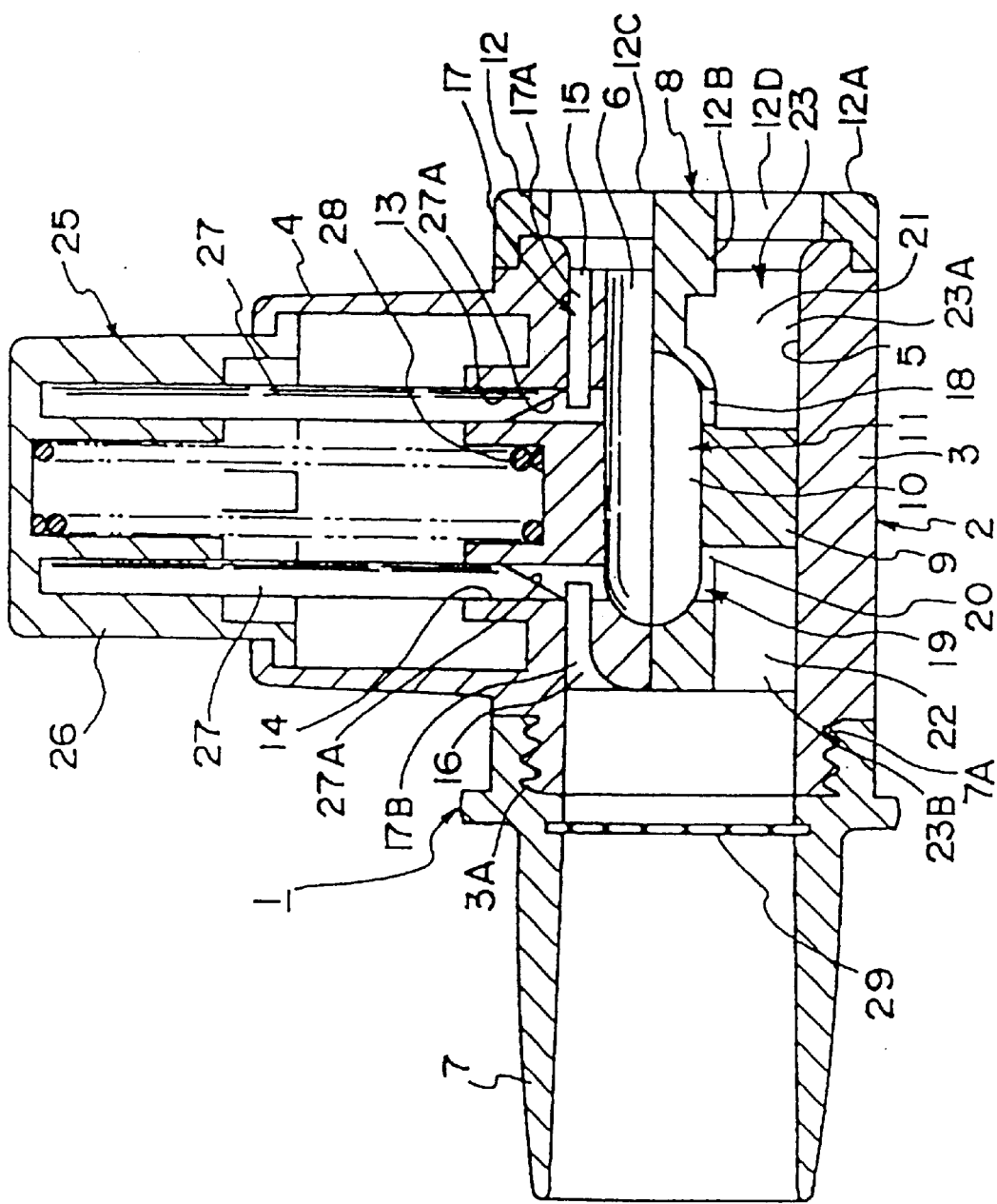
FIG. 1 is a cross-sectional view showing an inhaling type medicine administrating device according to a first embodiment of the present invention.

Hereinafter, respective embodiments of an inhaling type medicine administering device according to the present invention will be discussed in detail with reference to attached drawings.

First, a first embodiment of the present invention will be discussed with reference to FIGS. 1 to 9. 1 designates a medicine administering device main body. The medicine administering device main body 1 generally comprises a body 2, a suction mouth 7, and the like which will be discussed after.

2 designates the body which is located at one side of the medicine administering device main body 1 and forms the outer shape of the medicine administering device main body 1. The body 2 includes a cylindrical main body 3 which is formed generally cylindrical, and an elongate and cylindrical perforating tool guide 4 which is protruded upward from the outer peripheral surface of the cylindrical main body 3 and adapted to movably support a support section 26 of the perforating tool 25 which will be discussed after.

Additionally, the above-mentioned cylindrical main body 3 is formed with a threaded section 3A which is located at the other end side. A threaded section 7A of the suction mouth 7 is threadedly engaged with the threaded section 3A. Further, the cylindrical main body 3 is formed at its outer peripheral side with an inflow-side passage 15 and an outflow-side passage 16 discussed after, and at its inner peripheral side with a holder accommodating section 5.

Figure 2:
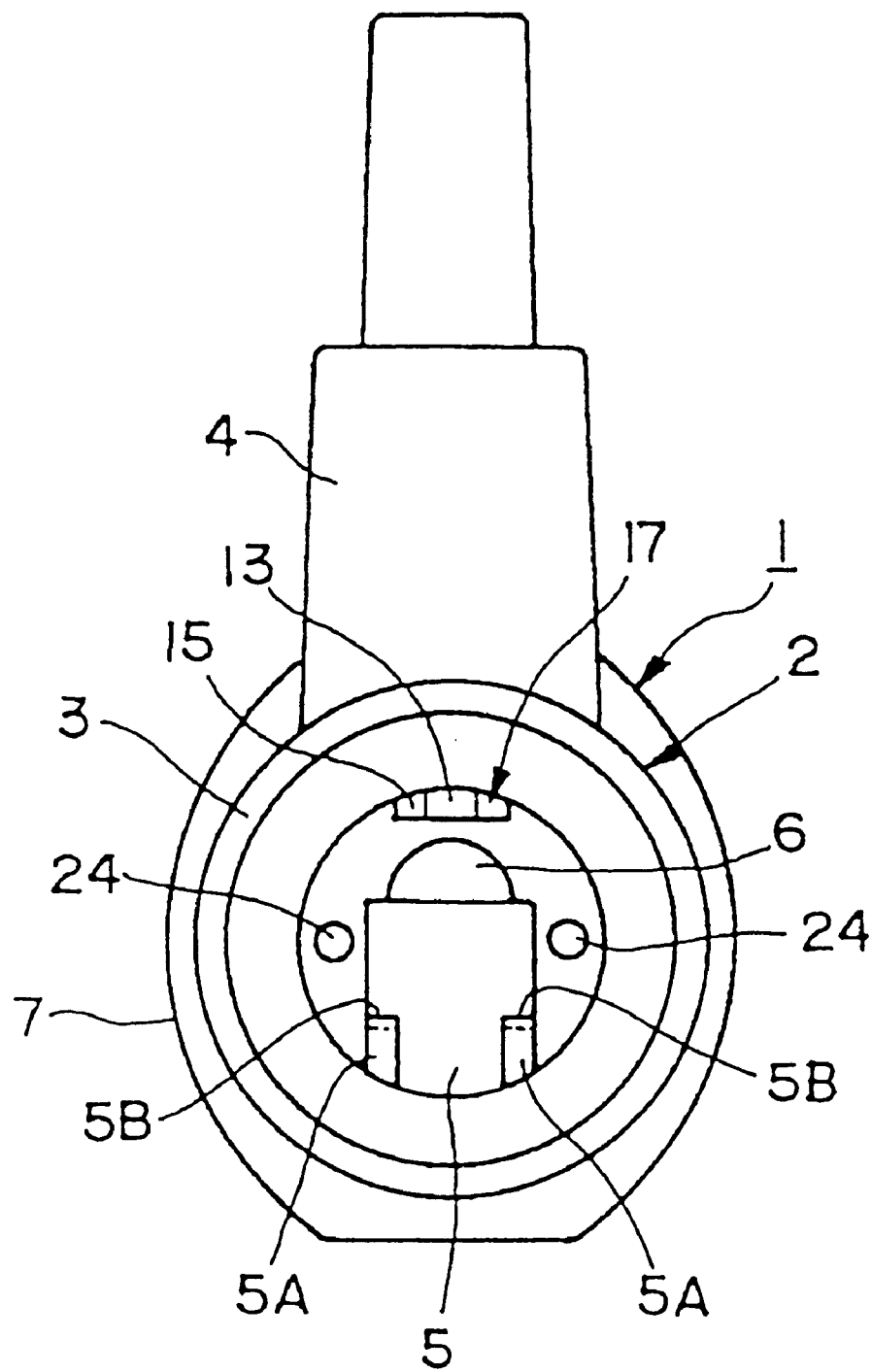
FIG. 2 is a right side view of the medicine administering device main body shown in FIG. 1.

5 designates the holder accommodating section which is formed at the inner peripheral side of the cylindrical main body 3 and accommodates therein a capsule holding section 9 of a capsule holder 8 (which will be discussed after) in such a manner that the capsule holding section 9 can get in and out. The holder accommodating section 5 is located one-sided to the lower-side of the cylindrical main body 3 and is formed as a generally rectangular through-hole which extends in the axial direction of the cylindrical main body 3, as shown in FIG. 2. Additionally, the holder accommodating section 5 is provided with step sections 5A, 5A which axially extend so as to be located at the lower sides of the side surfaces and project to face each other. Each step section 5A is formed at the upper surface side of one end section with an engagement projection 5B which is selectively engaged with a projection 9A or a projection 9B of the capsule holding section 9 (indicated by dotted lines in FIG. 7).

6 designates a capsule fitting groove which is formed to be located at the upper side of the holder accommodating section 5. The capsule fitting groove 6 forms a capsule holding space 11 in cooperation with a capsule fitting depression 10 which will be discussed after. The capsule fitting groove 6 is formed as a groove having a semicircular cross-section corresponding to the outer dimension of a capsule K in order to hold the capsule K fitted in the capsule fitting depression 10 from the upper side.

7 designates the suction mouth which is detachably installed to the other side of the cylindrical main body 3. The suction mouth 7 is formed generally cylindrical and is formed at its one end side with the threaded section 7A which is to be threadedly engaged with the threaded section 3A of the cylindrical main body 3. Additionally, the outer periphery at the other end side of the suction mouth 7 is formed to gradually decrease in diameter in a direction toward the other end side in order that a patient can easily hold the suction mouth 7 in his or her mouth.

8 designates the capsule holder which is detachably disposed to the medicine administering device main body 1. The capsule holder 8 generally includes the capsule holding section 9 and a grasping section 12 which will be discussed after.

Figure 3:
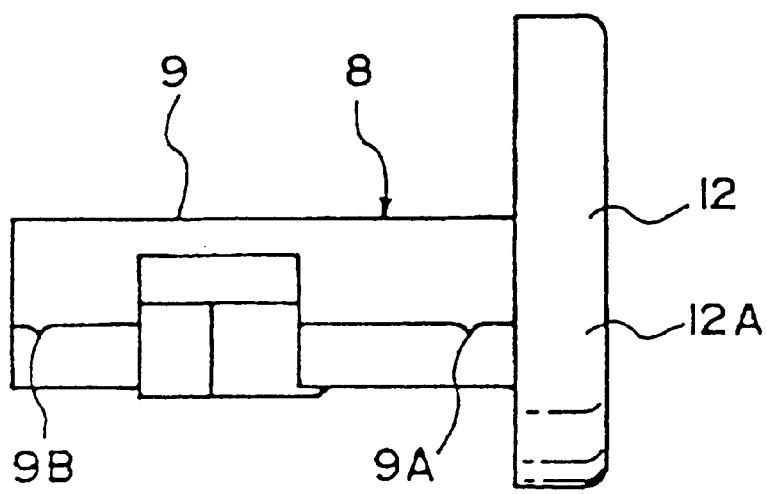
FIG. 3 is a front view of a capsule holder shown in FIG. 1.
Figure 4:
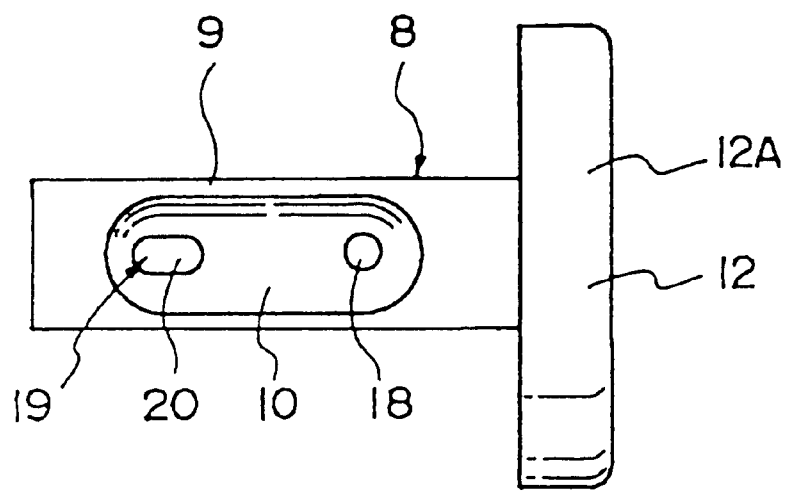
FIG. 4 is a plan view of the capsule holder.
Figure 5:
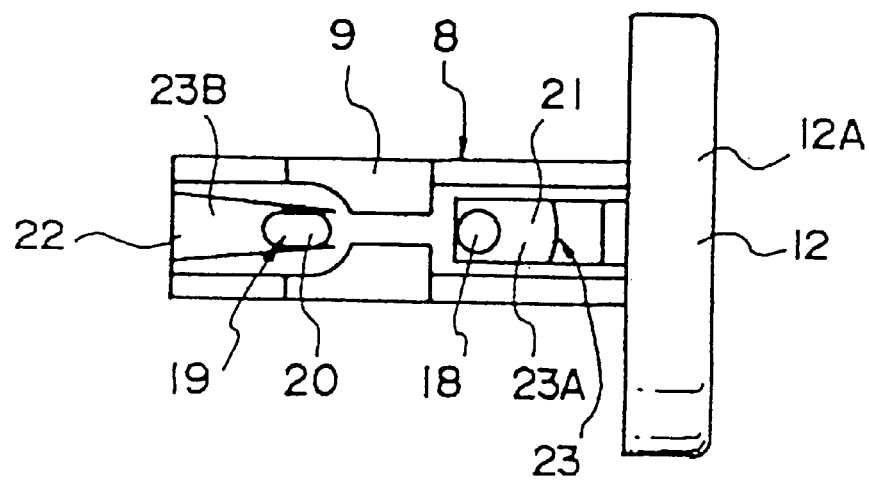
FIG. 5 is a bottom view of the capsule holder.

9 designates the capsule holding section which constitutes a main body of the capsule holder 8 and disposed in the holder accommodating section 5 to be capable of getting in and out. The capsule holding section 9 is formed having a generally T-shaped cross-section to be fitted in the holder accommodating section 5 (See FIG. 6). Additionally, as shown in FIG. 3, the capsule holding section 9 is provided with the projections 9A, 9B which are engageable with the engagement projection 5B of the holder accommodating section 5 and formed axially separate from each other to project downward.

Here, the above-mentioned projections 9A, 9A form a locating engagement section, in cooperation with the engagement projection 5B of the above-mentioned capsule accommodating section 5. The projection 9A is brought into engagement with the engagement projection 5B, at a pushed-in position where the capsule holding section 9 of the capsule holder 8 is the deepest pushed in the holder accommodating section 5 as shown in FIGS. 1, 8 and the like. Additionally, the projection 9B is brought into engagement with the engagement projection 5B at its drawn-out position (or a state shown in FIG. 7) where the capsule holding section 9 is drawn of the holder accommodating section 5 to such an extent that the capsule K can be installed and taken out after use.

Additionally, the engagement between the engagement projection 5B and the projection 9B is released by further drawing out the capsule holder 8 from the drawn-out position, so that the capsule holder 8 can be drawn and separated from the medicine administering device main body 1.

10 designates the capsule fitting depression formed in order that the capsule K is fitted at the upper surface side of the capsule holding section 9. The capsule fitting depression 10 is formed as a depressed groove having the semicircular cross-section so that the capsule K can be embedded in its lower part which is lower than its axis. The capsule fitting depression 10 forms the capsule holding space 11 for holding the capsule K, between it and the above-mentioned capsule fitting groove 6, at its pushed-in position where the capsule holding section 9 is pushed in the holder accommodating section 5.

Figure 6:
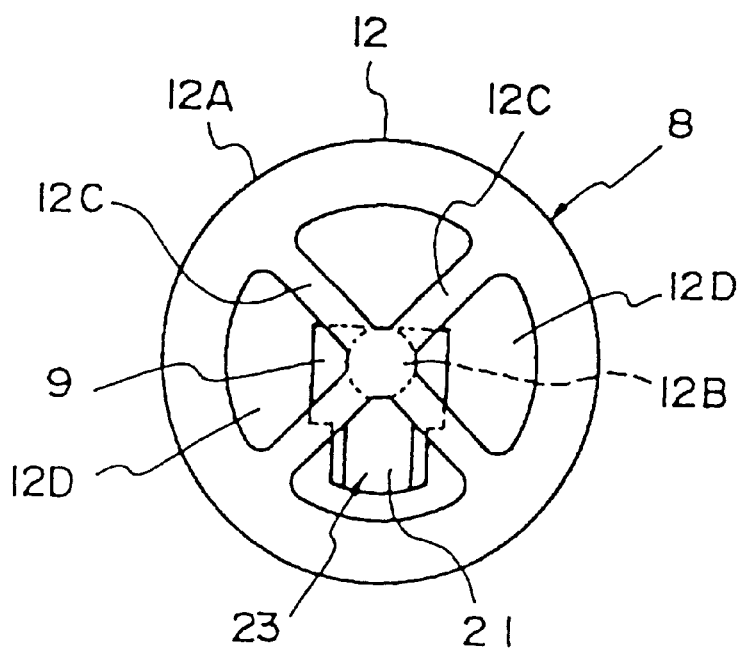
FIG. 6 is a right side view of the capsule holder.

12 designates the grasping section which is formed integral with the one side of the capsule holding section 9. As shown in FIG. 6, the grasping section 12 generally includes an annular member 12A having an outer diameter which is equal to that of the cylindrical main body 3, a shaft member 12B fixed to the capsule holding section 9, and four leg sections 12C, 12C, ... which are arranged cross-shaped to connect the shaft member 12B and the above-mentioned annular member 12A. Each of openings 12D, 12D, ... is formed between the above-mentioned leg sections 12C and forms part of each of air flow passages 17, 23 which will be discussed after.

In the thus formed capsule holder 8, the capsule holding section 9 can be located at the drawn-out position by drawing out the capsule holding section 9 upon grasping the outer periphery of the annular member 12A of the grasping section 12. At this drawn-out position, the capsule K filled with medicine can be fitted in the capsule fitting depression 10 of the capsule holding section 9, or the capsule K after use can be taken out of the capsule fitting depression 10. Additionally, by pushing the capsule holding section 9 in the holder accommodating section 5 upon grasping the grasping section 12 in a state where the capsule K is fitted in the capsule fitting depression 10 of the capsule holding section 9, the capsule holding section 9 is located at the pushed-in position so that the capsule K can be held in the capsule holding space 11.

Subsequently, 13 designates an inflow-side pin insertion hole which is opened to the capsule fitting groove 6 at a position near the one side of the capsule fitting groove 6. The pin insertion hole 13 is located inside the perforating tool guide 4 and formed extending radially in the cylindrical main body 3.

Additionally, 14 designates an outflow-side pin insertion hole which is opened to the capsule fitting groove 6 at a position near the other side of the groove 6. The pin insertion hole 14 is located inside the perforating tool guide 4 to be parallel with the inflow-side pin insertion hole 13 and formed extending radially in the cylindrical main body 3.

15 designates the inflow-side passage formed at the outer peripheral side of the cylindrical main body 3. The one side of the inflow-side passage 15 is opened to atmospheric air through each opening 12D, while the other side of the inflow-side passage 15 is in communication with the inflow-side pin insertion hole 13.

16 designates the outflow-side passage formed at the outer peripheral side of the cylinder main body 3. The one side of the outflow-side passage 16 is in communication with the outflow-side pin insertion hole 14, while the other side of the outflow-side passage 16 is opened to the side of the suction mouth 7.

Here, 17 designates the first air flow passage formed in the cylindrical main body 3. The first air flow passage 17 generally includes an inflow-side air flow passage 17A having the pin insertion hole 13 and the inflow-side passage 15, and an outflow-side air flow passage 17B having the pin insertion hole 14 and the outflow-side passage 16. Subsequently, 18 designates an inflow-side pin insertion hole which is formed in the capsule holding section 9 of the capsule holder 8 and opened near the one side of the capsule fitting depression 10. The pin insertion hole 18 is formed coaxial and aligned with the pin insertion hole 13.

19 designates an outflow-side pin insertion hole which is formed in the capsule holding section 9 of the capsule holder 8 and opened near the other side of the capsule fitting depression 10. The pin insertion hole 19 is located at the other side and formed as an elongate hole which has an arcuate section coaxial with the pin insertion hole 14 and elongates toward the one side in the axial direction of the capsule fitting depression 10. Additionally, the pin insertion hole 19 includes a burr releasing space 20 which is located at one side of the hole 19 so as to face an inclined face 27A formed at the tip end side of a pin 27.

Figure 9:
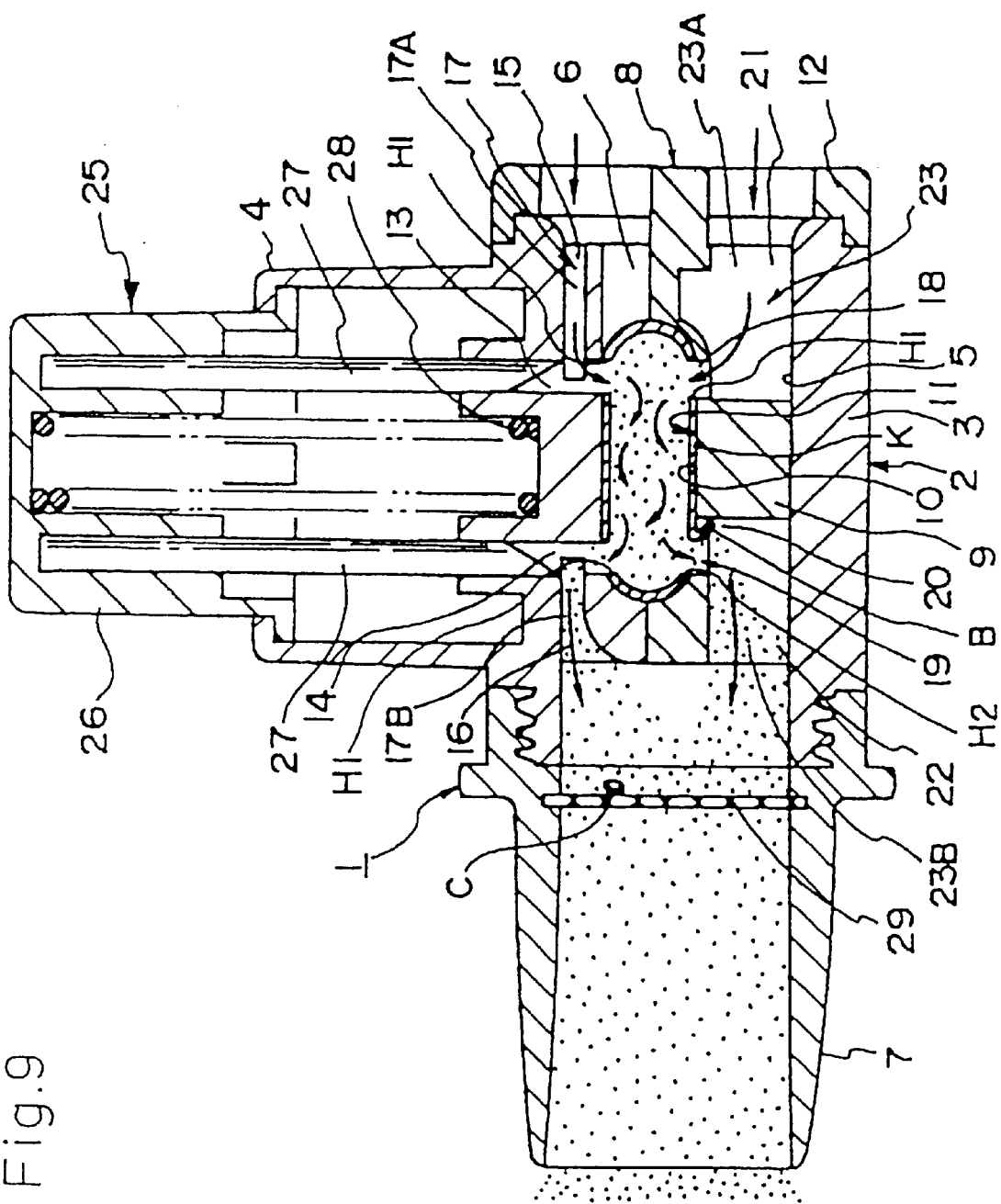
FIG. 9 is a cross-sectional view showing the inhaling type medicine administering device in a state where medicine within the capsule is inhaled.
Figure 10:
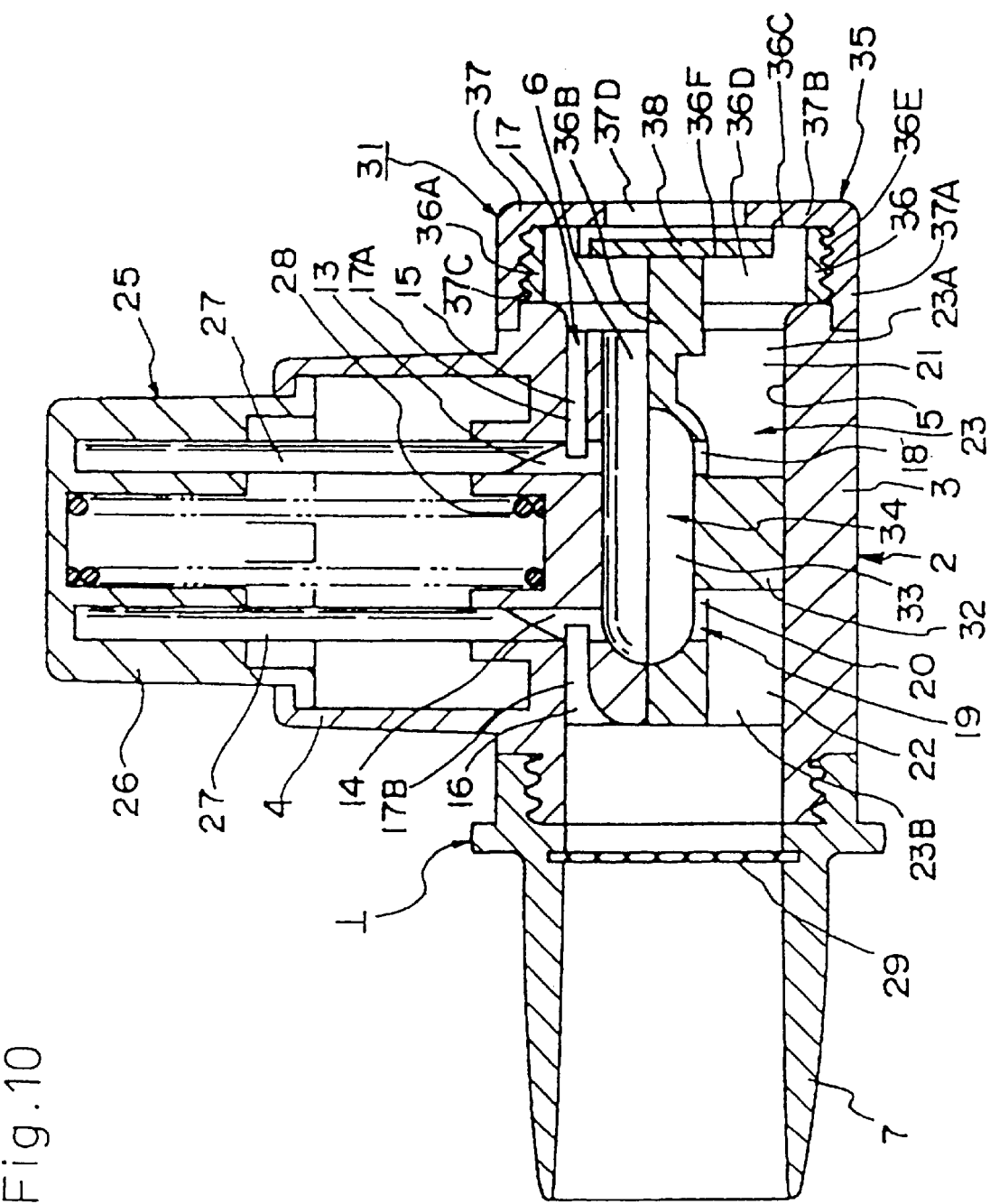
FIG. 10 is a cross-sectional view showing the inhaling type medicine administering device according to a second embodiment of the present invention.

Here, as shown in FIG. 9, the above-mentioned burr releasing space 20 allows burr B to bend in a state where the burr B is left integral with the capsule K, when a hole H2 communicated with the pin insertion hole 19 is formed in the capsule K with the pin 27.

21 designates an inflow-side passage which is located at the lower side of the capsule holding section 9 and formed between the capsule holding section 9 and the cylindrical main body 3. The one side of the inflow-side passage 21 is opened to atmospheric air through each opening 12D, while the other side of the inflow-side passage 21 is in communication with the inflow-side pin insertion hole 18.

22 designates an outflow-side passage which is located at the lower side of the capsule holding section 9 and formed between the capsule holding section 9 and the cylindrical main body 3. The one side of the outflow-side passage 22 is in communication with the outflow-side pin insertion hole 19, while the other side of the outflow-side passage 9 is opened to the side of the suction mouth 7.

Here, 23 designates the second air flow passage which is formed in the capsule holding section 9 of the capsule holder 8. The second air flow passage 23 generally includes an inflow-side air flow passage 23A having the pin insertion hole 18 and the inflow-side passage 21, and an outflow-side air flow passage 23B having the pin insertion hole 19 and the outflow-side passage 22.

24, 24 designate respectively two auxiliary air flow passages (shown in FIG. 2) which are formed respectively at positions which shift an angle of 90 degrees relative to the air flow passages 17, 23. The two auxiliary air flow passages 24, 24 are formed piercing axially the cylindrical main body 3. Each auxiliary air passage 24 functions to cancel difficulty in breathing during patient's breathing-in by increasing a flow amount of air flowing when the patient breathes in.

Further, 25 designates the perforating tool to perforate the capsule K. The perforating tool 25 generally includes the supporting section 26 which is movably supported inside the perforating tool guide 4, the pins 27, 27 whose tip end sides are located in the pin insertion holes 13, 14 and whose base end sides are fixed to the supporting section 26, and a return spring 28 disposed between the above-mentioned supporting section 26 and the cylindrical main body 3. The above-mentioned return spring 28 biases the supporting section 26 in a direction in which the pins 27, 27 get away from the capsule K, and returns the supporting section 26 and the pins 27, 27 to their initial positions after the capsule K are perforated. Additionally, the above-mentioned pins 27, 27 are respectively formed at their tip end side with the inclined faces 27A, 27A. The pins 27, 27 are installed to the supporting section 26 in such a manner that the inclined faces 27A, 27A face each other.

Here, when the hole H2 in communication with the capsule insertion hole 19 is formed by the pin 27 located at the side of the suction mouth 7, the burr B formed during this perforation action is bent to enter the burr releasing space 20 by the inclined face 27A so as to be accommodated in the burr releasing space 20.

Such a perforating tool 25 functions as follows: By inserting the respective pins 27, 27 into the pin insertion holes 13, 14 and the likes upon pushing the supporting section 26 into the perforating tool guide 4 against the bias of the return spring 28, the inclined faces 27A, 27A at their tip end sides of the pins 27, 27 are inserted into the capsule K in the capsule holding section 9 so that radially piercing holes H1, H1, H1 and H2 are formed. When a depressing force to the supporting section 26 is removed, the supporting section 26, the respective pins 27, 27 move backward to their initial positions.

29 designates a mesh member disposed inside the suction mouth 7. The mesh member 29 is formed circular by weaving fine wires into a mesh. The outer peripheral side of the mesh member 29 is fixed to the inner peripheral side of the suction mouth 7. The mesh member 29 functions to pulverize medicine and trap foreign matters such as broken piece C of the capsule K and the like as shown in FIG. 9 by causing medicine passing through the suction mouth 7 to strike against the mesh member 29.

The inhaling type medicine administering device according to this embodiment has an arrangement as discussed above. Next, discussion will be made on a preparation operation made before the patient inhales medicine and on flow of air and medicine during inhalation of medicine.

Figure 7:
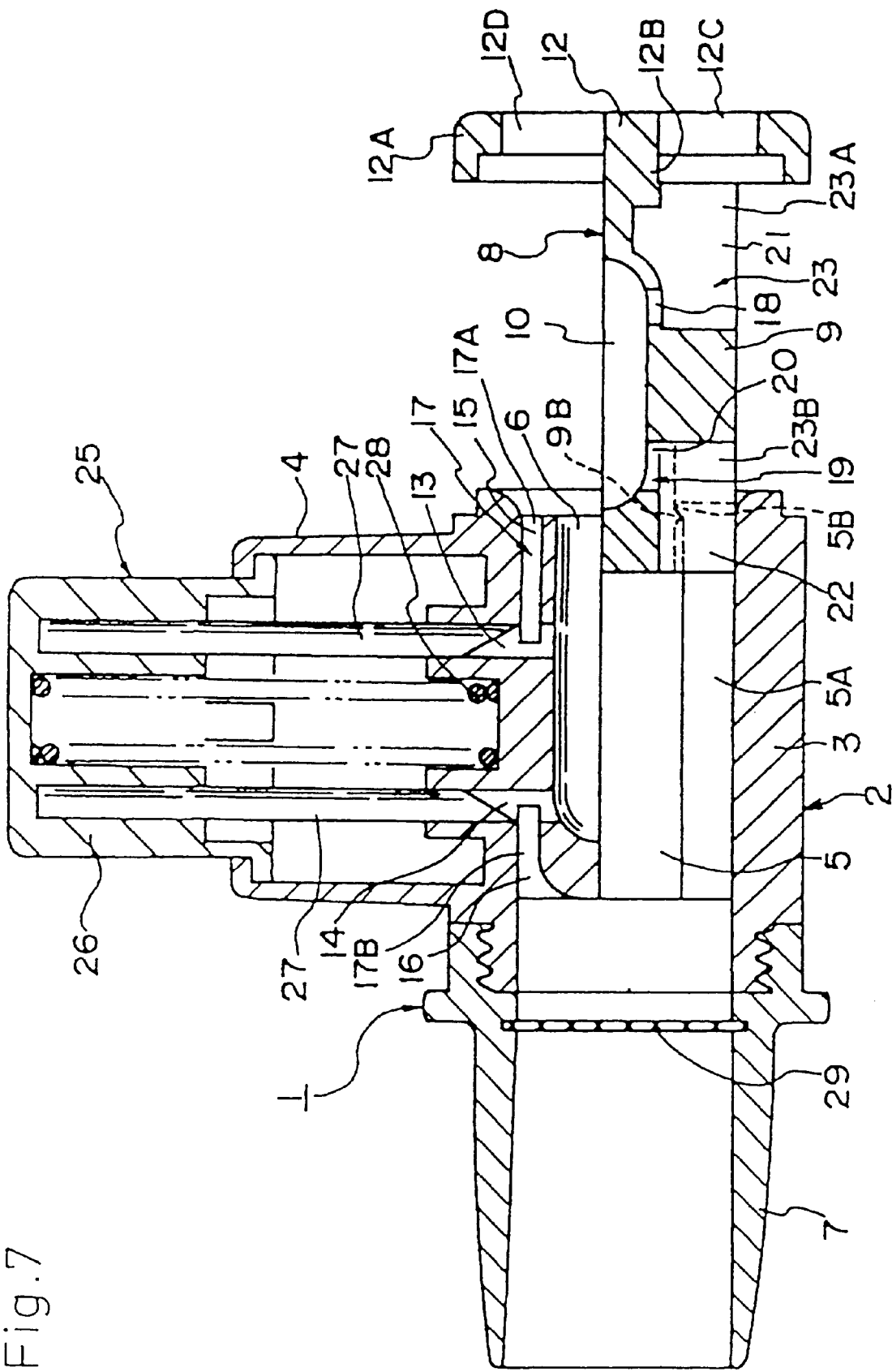
FIG. 7 is a cross-sectional view showing the inhaling type medicine administering device in a state where the capsule holder is located at a drawn-out position.
Figure 8:
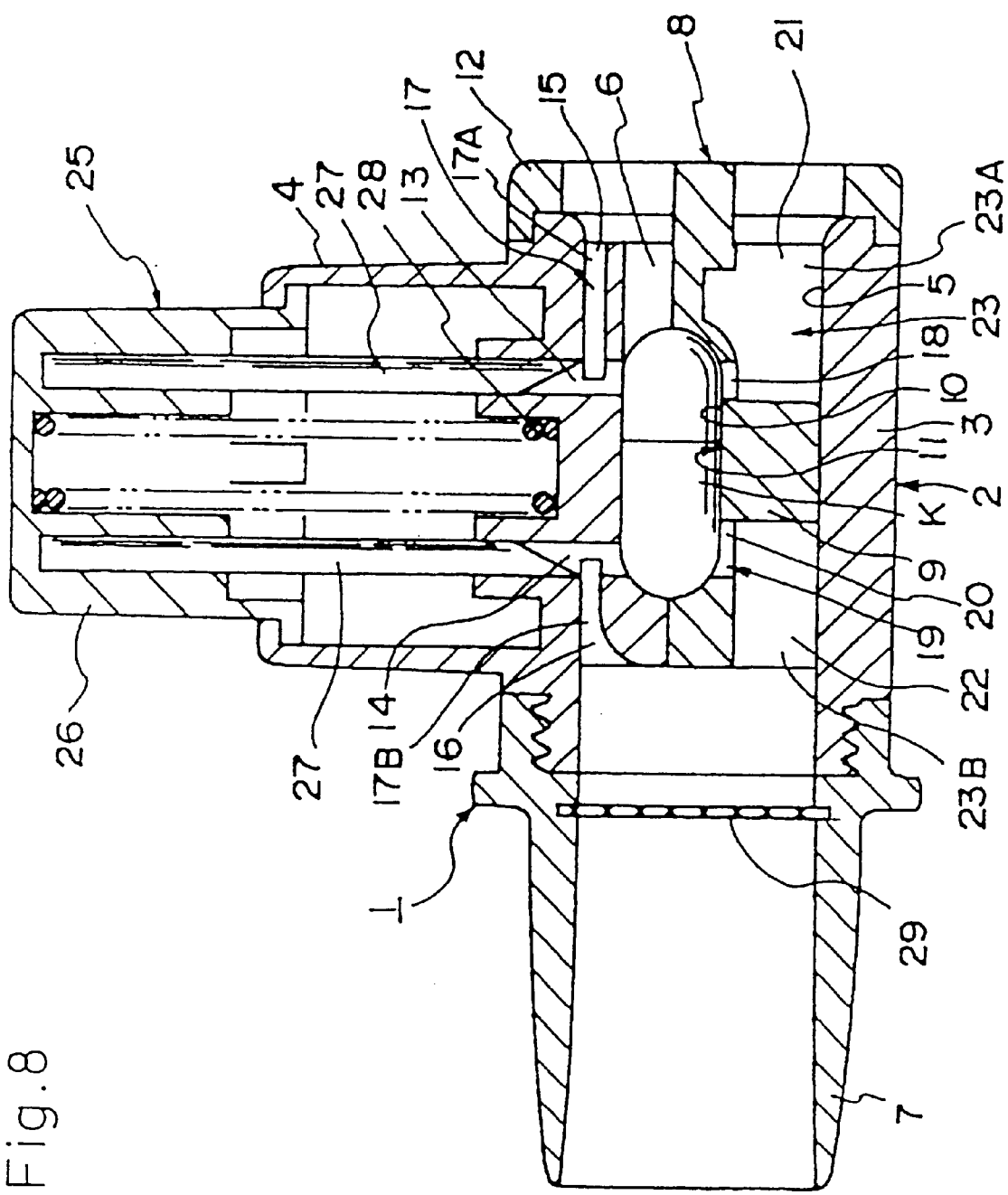
FIG. 8 is a cross-sectional view showing the inhaling type medicine administering device in a state where the capsule holder is located at a pushed-in position where a capsule is held in a capsule holding space.

First, as shown in FIG. 7, the grasping section 12 is grasped, and the capsule holding section 9 is drawn out of the holder accommodating section 5. During drawing-out of this capsule holder 8, the projection 9B formed in the capsule holding section 9 is brought into engagement with the engagement projection 5B of the holder accommodating section 5 at the drawn-out position, and therefore the capsule holder 8 can be prevented from separating from the medicine administering device main body 1.

When the capsule holder 8 is put into the drawn-out position, the capsule K is fitted in capsule fitting depression 10 of the capsule holding section 9, and thereafter the capsule holding section 9 is pushed in the holder accommodating section 5 upon grasping the grasping section 12. By this, the capsule K is located at the pushedin position and held in capsule holding space 11 under a state where the capsule K is pressed from the upper side by the capsule fitting groove 6, as shown in FIG. 8. Additionally, under a state where the capsule K is located at the pushed-in position, the projection 9A of the capsule holding section 9 is brought into engagement with the engagement projection 5B, so that the capsule holder 8 is prevented from being getting out.

Subsequently, when the capsule K is put into the pushed-in position, the respective pins 27 are thrust through the insertion holes 13, 14; 18, 19, so that the respective pins 27 pierce the capsule K.

Here, perforation for the capsule K will be discussed. When the pin 27 at the side of the grasping section 12 pierces the capsule K, the hole H1 in communication with the pin insertion hole 13 and the hole H1 in communication with the pin insertion hole 18 are successively formed in the capsule K.

Additionally, when the pin 27 at the side of the suction mouth 7 pierces the capsule K, the hole H1 in communication with the pin insertion hole 14 is formed, and thereafter the hole H2 in communication with the pin insertion hole 19 is formed. However, during formation of this hole H2, burr B of the capsule K is bent to the side of the burr releasing space 20 under the action of the inclined face 27A of the pin 27 and accommodated in the burr releasing space 20 for the reasons why the pin insertion hole 19 has the burr releasing space 20, and the tip end side of the pin 27 is formed with the inclined face 27A to be faced to the burr releasing space 20.

By this, the hole H2 can be formed in the capsule K without causing separation of the burr B from the capsule K, thereby simplifying cleaning operation and the like, while preventing the patient from having a coughing fit during inhaling medicine.

After the four holes H1, H1, H1, H2 are formed in the capsule K, the supporting section 26 and the respective pins 27, 27 return to their initial position under the biasing force of the return spring 28.

Next, discussion will be made on flow of air and medicine within the inhaling type medicine administering device at the time when the patient inhales medicine, with reference to FIG. 9.

First, the patient holds the other end side of the suction mouth 7 in his or her mouth, and breathes in under this condition. By this, as indicated by arrows in FIG. 9, air flows from the respective openings 12D of the grasping section 12 through inflow-side air flow passages 17A, 23A to the side of capsule K, and then from the inflow-side holes H1, H1 into the capsule K. Air flown into the capsule K spreads granular medicine filled in the capsule K so as to mix medicine into air.

Air which thus contains medicine in the capsule K is released from the outflow-side holes H1, H2 through the outflow-side air flow passages 17B, 23B to the side of the suction mouth 7, and then sucked into the lungs of the patient from the suction mouth 7 through the inside of the mouth and the trachea of the patient. Thus, medicine can be administered into the lungs of the patient.

Additionally, during such inhaling medicine, medicine flown out from the outflow-side air flow passages 17B, 23B strike against the mesh member 29 to be pulverized, so that medicine can be effectively sucked into the lungs of the patient. Furthermore, even if broken piece C of the capsule K and the like produced during perforation of the capsule K flows out to the side of the suction mouth 7, this broken piece C can be caught by the mesh member 29, so that the patient can inhale only medicine.

When an inhaling operation for medicine within the capsule K is completed, the capsule holding section 9 of the capsule holder 8 is drawn out of the holder accommodating section 5 upon grasping the grasping section 12 thereby putting the capsule holding section 5 into the drawn-out position. By this, the capsule K after use can be taken out of the capsule holder 8.

Accordingly, according to this embodiment, by disposing the capsule holding section 9 of the capsule holder 8 in such a manner as to be able to get in or get out of the holder accommodating section 5 of the cylindrical main body 3, the capsule K can be installed in the capsule fitting depression 10, and the capsule K after use can be taken out, at the drawn-out position where the capsule holding section 9 is drawn out. Additionally, the capsule K can be held in the capsule holding space 11 at the pushed-in position where the capsule holding section 9 is pushed into the holder accommodating section 5.

Accordingly, such operations as installing the capsule K to the capsule holder 8 and taking out the capsule K after inhaling medicine can be easily accomplished without decomposing respective parts like in the conventional technique. The medicine administering device can be improved in operationability during the preparation operation for medicine administration while making easy usage of the inhaling type medicine administering device.

Additionally, since the capsule holder 8 is provided with the grasping section 13 which is to be grasped when the capsule holding section 9 is gets in or out, the capsule K can be installed or taken out without the patient's contact to the capsule holding section 9, the air flow passages 17, 23, and the like, so that the medicine administering device can be improved from a sanitary view point.

Additionally, the holder accommodating section 5 is provided with the engagement projection 5B, and the capsule holding section 9 is provided with the projections 9A, 9A to which the engagement projection 5B is to be selectively engaged. Accordingly, the capsule holding section 9 can be located at the pushed-in position shown in FIGS. 1 and 8, and at the drawn-out position shown in FIG. 7. By this, the pin insertion holes 13, 14, 18, 19 can be readily located under a condition where the capsule holding section 9 is at the pushed-in position, while preventing the capsule holder 8 from falling off at the drawn-out position thereby preventing the capsule holder 8 from being lost and damaged or the like.

Further, the capsule holder 8 can be separated from the medicine administering device main body 1 by drawing the capsule holder 8 out of the medicine administering device main body 1 against the engagement between the engagement projection 5B of the holder accommodating section 5 and the projection 9B of the capsule holding section 9. Consequently, the inside of the holder accommodating section 5, the capsule holder 8, and the like can be effectively rinsed. Also in this regard, the medicine administering device can be improved from a sanitary viewpoint and can be readily treated.

Next, a second embodiment of the present invention will be discussed with reference to FIGS. 10 to 14. This embodiment features to be arranged such that the capsule holder is provided with a reverse-flow preventing valve for allowing air flows through the air flow passage toward the suction mouth and for impeding flow in the reverse direction. In this embodiment, the same reference numerals are assigned to the same component elements as those in the first embodiment, thereby omitting explanation thereof.

31 designates a capsule holder according to this embodiment, used in place of the capsule holder 8 according to the first embodiment. The capsule holder 31 generally includes a capsule holding section 32, a grasping section 35, and the like.

32 designates the capsule holding section serving as a main body of the capsule holder 31. Similarly to the capsule holding section 9 in the first embodiment, the capsule holding section 9 is formed to have a generally T-shaped cross-section to be fitted in the holder accommodating section 5. The capsule holding section 5 is formed at its upper surface side with a capsule fitting depression 33 in which the capsule K is to be fitted, in which a capsule holding space 34 is formed between the capsule fitting depression 33 and the capsule fitting groove 6. Additionally, the capsule holding section 32 is formed with the second air flow passage 23 which includes the inflow-side air flow passage 23A having the pin insertion hole 18 and the inflow-side passage 21, and the outflow-side air flow passage 23B having the pin insertion hole 19 and the outflow-side passage 22.

Figure 11:
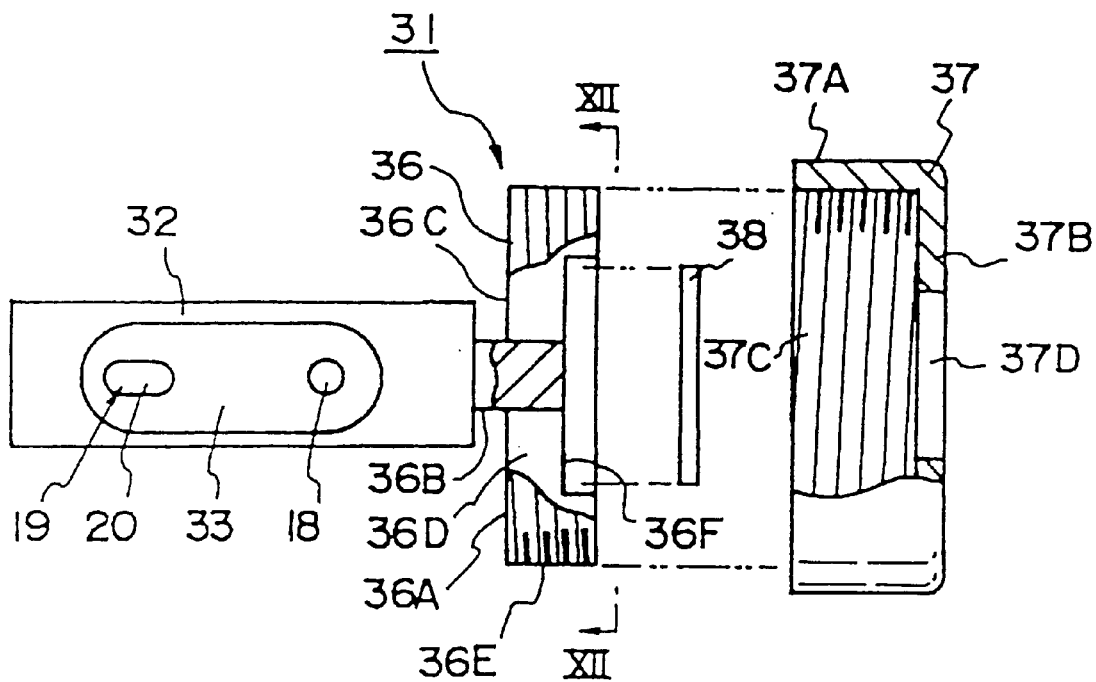
FIG. 11 is an external appearance view, partly in section, showing an exploded state for the capsule holder and a check valve in FIG. 10.
Figure 12:
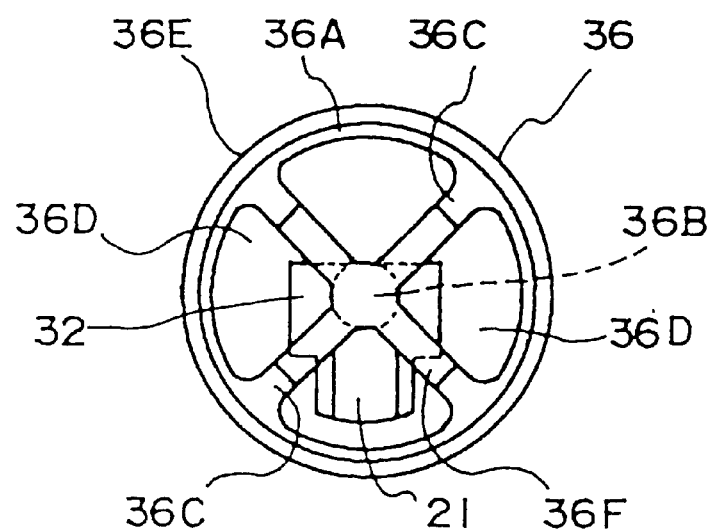
FIG. 12 is a right side view of the capsule holder in a state where a cap is removed, as viewed in the direction of arrows VII—VII of FIG. 11.

35 designates the grasping section which is formed integral with the one side of the capsule holding section 32. The grasping section 35 generally includes a supporting ring 36 and a cap 37 which will be discussed after. 36 designates the supporting ring which is formed integral with the one side of the capsule holding section 32. As shown in FIGS. 11 and 12, the supporting ring 36 generally includes an annular member 36A of the annular shape, a shaft member 36B fixed to the capsule holding section 23, and four leg sections 36C, 36C, . . . which are arranged cross-shaped to connect the shaft member 36B and the above-mentioned annular member 36A. Each of openings 36D, 36D, . . . is formed between the above-mentioned leg sections 36C and forms part of each of the air flow passages 17, 23. Additionally, the above-mentioned annular member 36A is formed at its outer peripheral side with a threaded section 36E. The shaft member 36B and each leg section 36C are formed at their one side surface with a depression section 36F in which a check valve 38 discussed after is movably disposed.

37 designates a cap disposed to cover the supporting ring 36. The cap 37 includes a cylindrical section 37A and a lid section 37B and is formed into the shape of a cylinder with a lid. The cylindrical section 37A is formed at its inner peripheral side with a threaded section 37C which is to be threadedly engaged with the threaded section 36E of the supporting ring 36. Additionally, the lid section 37B is formed at its central portion with an air flow hole 37D constituting part of the air flow passages 17, 23.

38 designates a check valve serving as a reverse-flow preventing valve, disposed between the depression section 36F of the supporting ring 36 and the lid section 37B of the cap 37. The check valve 38 is formed disc-shaped so as to open or close the air flow hole 37D. The check valve 38 is opened during inhalation of medicine so as to allow air to flow through the air flow hole 37D toward the side of the suction mouth 7, and closed when air flow in the reverse flow is generated inside the suction mouth 7.

The second embodiment is thus arranged. In the second embodiment, generally the same functions and effects as those in the first embodiment can be obtained.

In this embodiment, when medicine is inhaled, the capsule holding section 32 is pushed in the holder accommodating section 5 under a condition where the capsule K is fitted in the capsule fitting depression 33, and then the respective holes H1, H2 are formed in the capsule K by the perforating tool 25, as the preparation operation.

Figure 13:
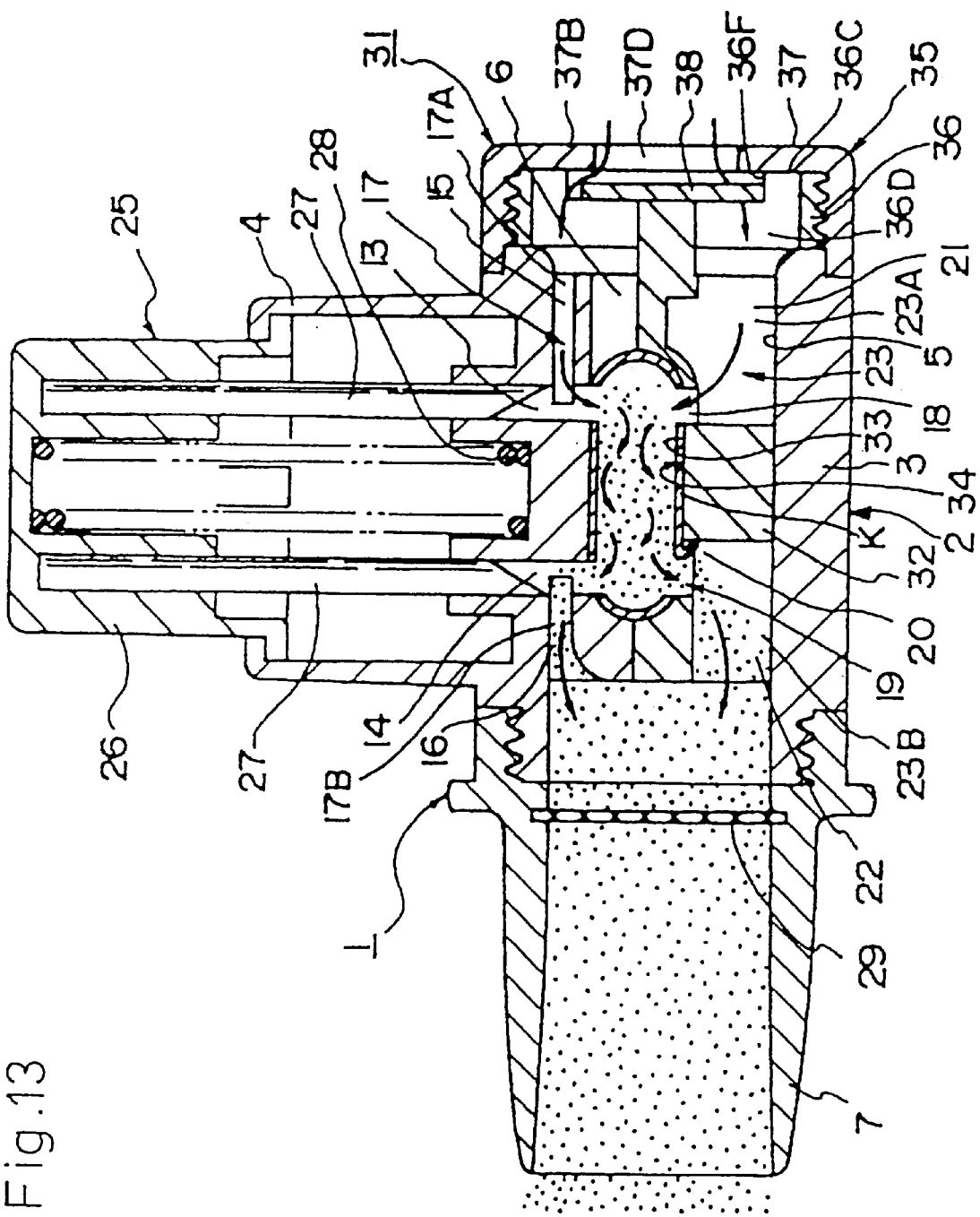
FIG. 13 is a cross-sectional view showing the inhaling type medicine administering device in a state where medicine within the capsule is inhaled.

When the preparation operation has been completed, the patient holds the suction mouth 7 in his or her mouth and breathes in. At this time, as shown in FIG. 13, the check valve 38 is separated from the lid section 37B under the action of the outside air flowing through the air flow holes 37D of the cap 37, and therefore medicine within the capsule K can be flown to the side of the suction mouth 7 so that medicine can be administered to the patient.

Figure 14:
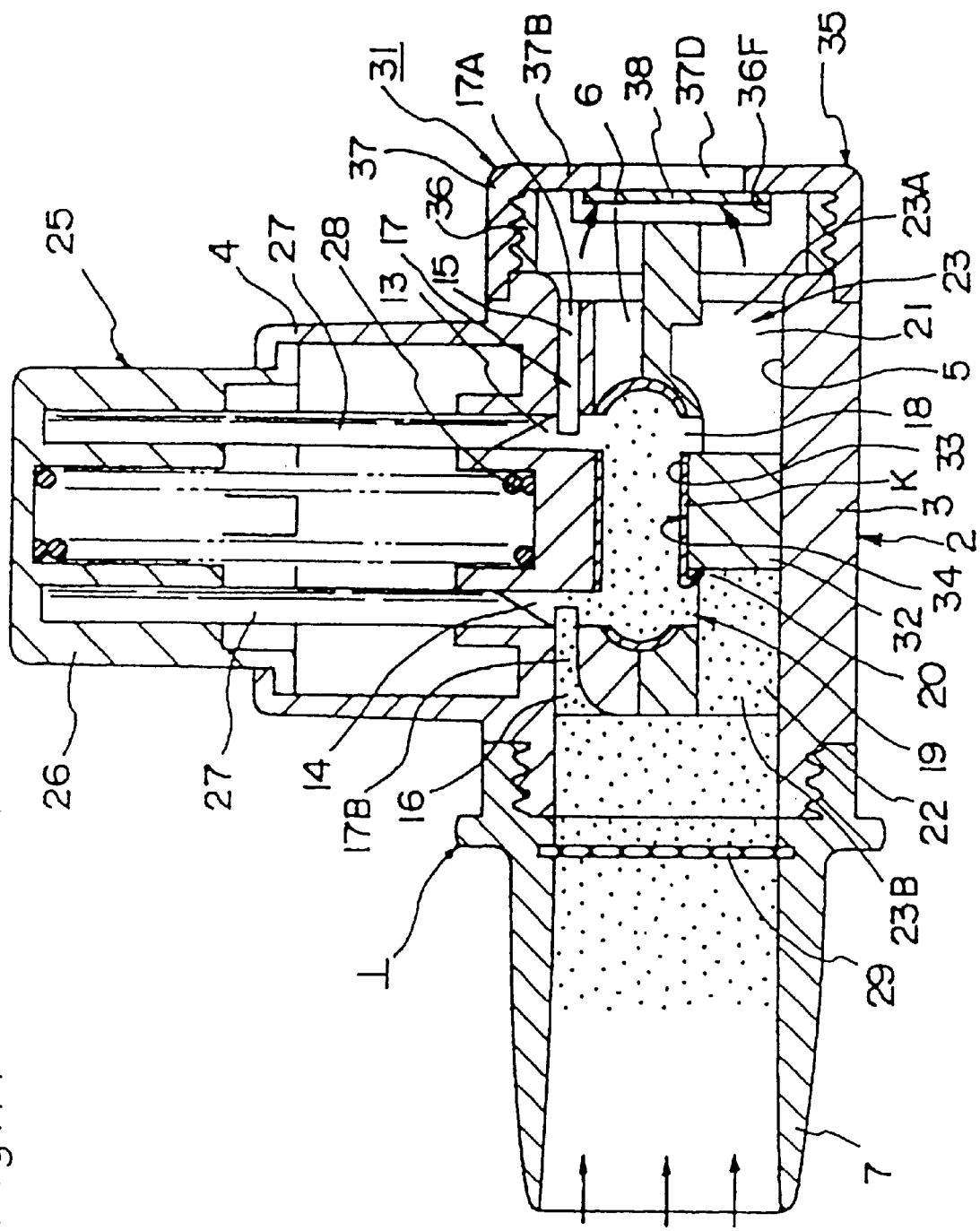
FIG. 14 is a cross-sectional view showing the inhaling type medicine administering device in a state where air reversely flows into a suction mouth.
Figure 15:
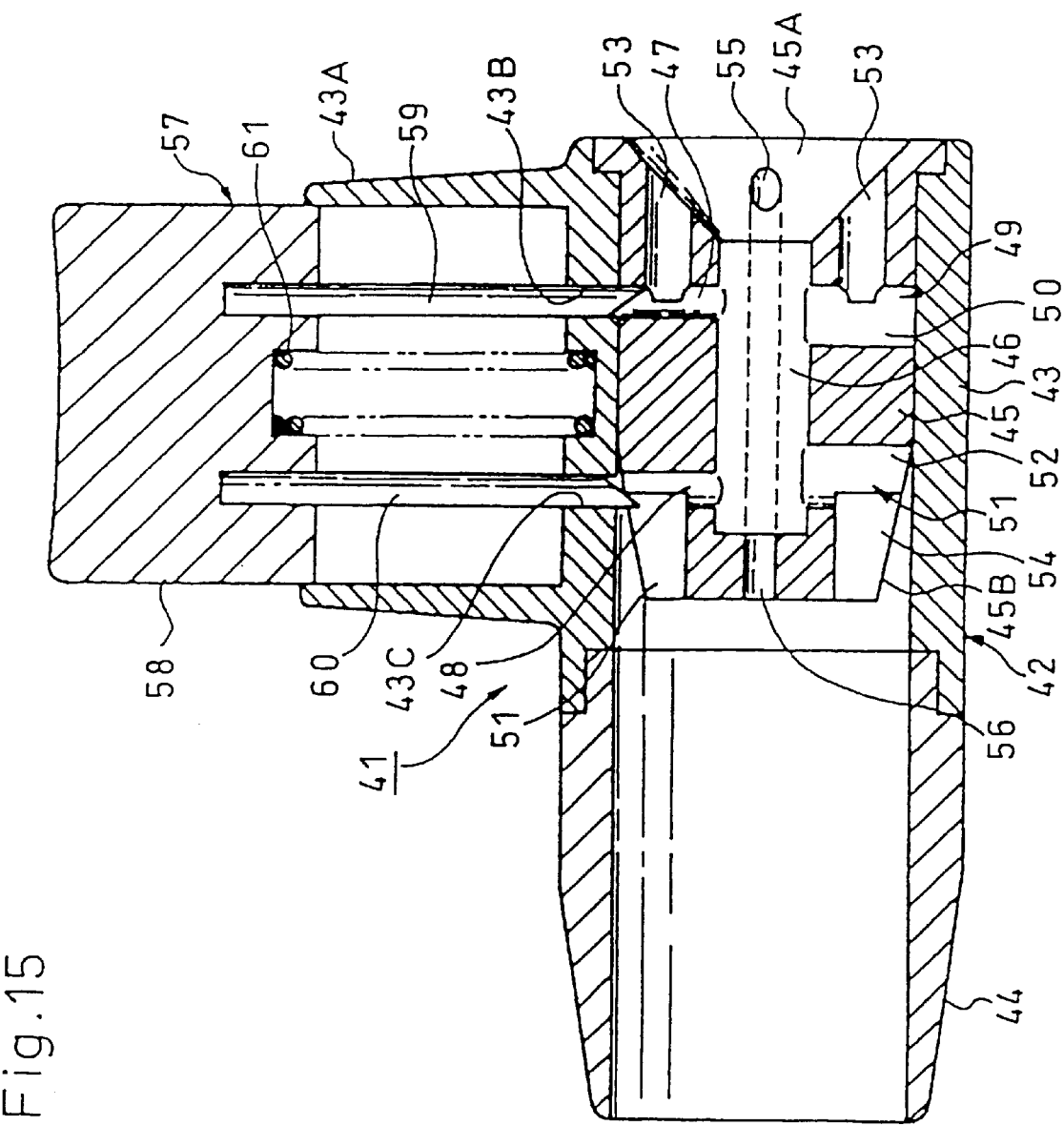
FIG. 15 is a cross-sectional view showing the inhaling type medicine administering device according to a third embodiment of the present invention.

When the patient has a coughing fit in the course of inhalation of medicine so that air is reversely flown into the suction mouth 7 as shown in FIG. 14, this reversely flown air causes the check valve 38 to contact with the lid section 37B of the cap 37 thereby blocking the air flow hole 37D. Consequently, medicine within the capsule K and the like can be prevented from being released out under the influence of the reversely flown air.

When the capsule holding section 32 of the capsule holder 31 is gotten in or out of the holder accommodating section 5, the capsule holding section 32 is gotten in or out by grasping the cap 37 of the grasping section 35. In this point, this embodiment is arranged as same as the above-mentioned first embodiment.

Therefore, according to this invention, even in case that the patient has a coughing fit in the course of inhalation of medicine, medicine within the capsule K and the like can be prevented from being released to the outside, so that a predetermined amount of medicine filled in the capsule K can be inhaled to the patient thereby effectively administering medicine to the patient.

While the above-mentioned second embodiment has been discussed using an example in which the check valve 38 is formed as a disc-shaped valve member, this invention is not limited to this, so that, for example, the check valve may be formed as other valve members such as flap valve and the like.

Additionally, while the above-mentioned respective embodiments have been discussed using examples in which the grasping section 12, 35 of the capsule holder 8, 31 is formed annular, this invention is not limited to this, so that, for example, the shaft member 12B, 36B may be axially extended to form a knob for grasping; or the grasping section may be formed into other shapes if it can be gotten in or out of the capsule holding section.

Next, a third embodiment of the present invention will be discussed with reference to FIGS. 15 to 20. In the drawings, 41 designates a medicine administering device main body serving as a base section of the inhaling type medicine administering device. The medicine administering device main body 41 includes a suction piece 42 and a capsule holder 45 which will be discussed after.

42 designates the suction piece which is formed generally cylindrical. The suction piece 42 generally includes a holder accommodating section 43 which is located at one side of the suction piece 42 and holds thereinside a capsule holder 45 which is inserted, and a suction mouth 44 disposed at the other side of the holder accommodating section 43. The above-mentioned holder accommodating section 43 is provided at its outer peripheral side with a guide cylindrical section 43A which is formed projecting radially outward to movably support a supporting section 58 of a perforating tool 57 which will be discussed after. Additionally, the holder accommodating section 43 is formed with pin holes 43B, 43C which are located within the above-mentioned guide cylindrical section 43A and are piercingly formed radially and axially separate from each other. Additionally, the above-mentioned suction mouth 4 is detachably fitted to the other end section of the holder accommodating section 43, in which the outer periphery at the other end side of the suction mouth 7 is formed to gradually decrease in diameter in a direction toward the other side in order that a patient can easily hold the suction mouth 7 in his or her mouth.

Figure 16:
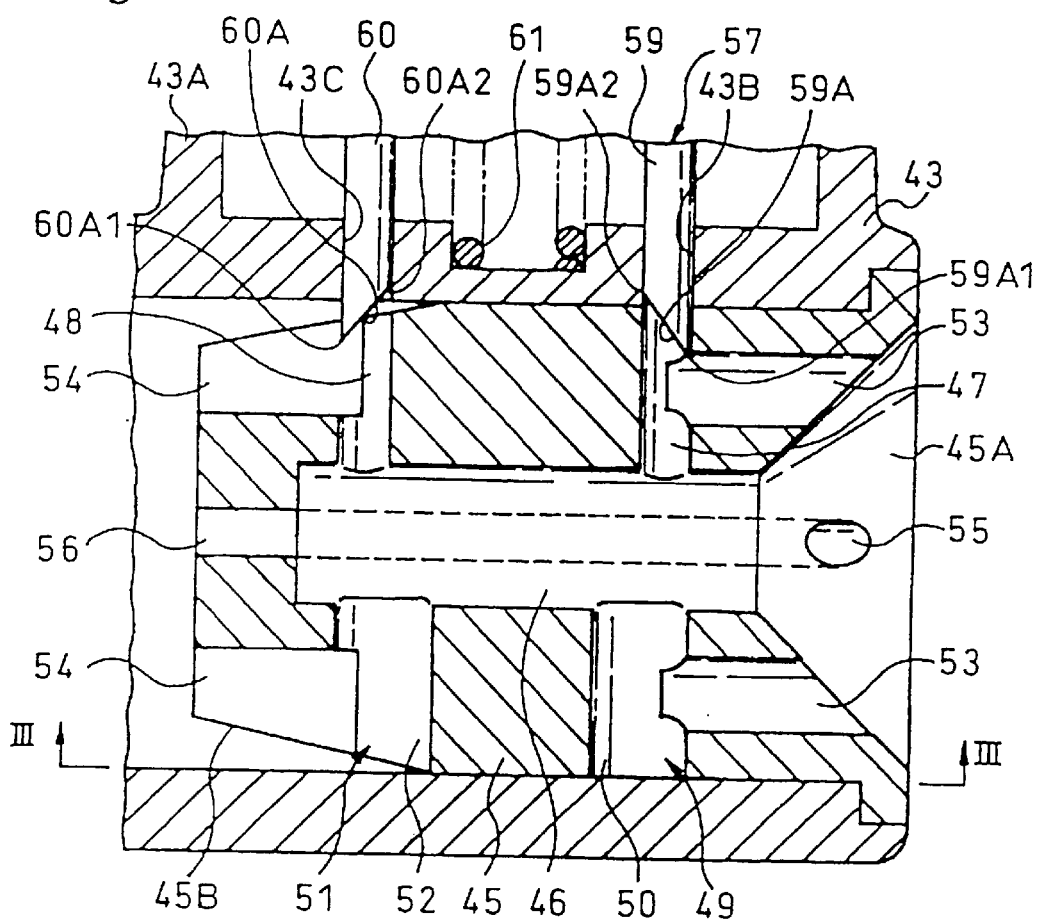

45 designates a capsule holder installed within the holder accommodating section 43. The capsule holder 45 is formed generally cylindrical as shown in FIG. 16, and is formed at its one end side with an inflow-side depression 45A which is tapered and gradually decreases in diameter. The capsule holder 45 is formed at the outer peripheral surface on the other end side with an outflowside tapered surface 45B.

Figure 18:
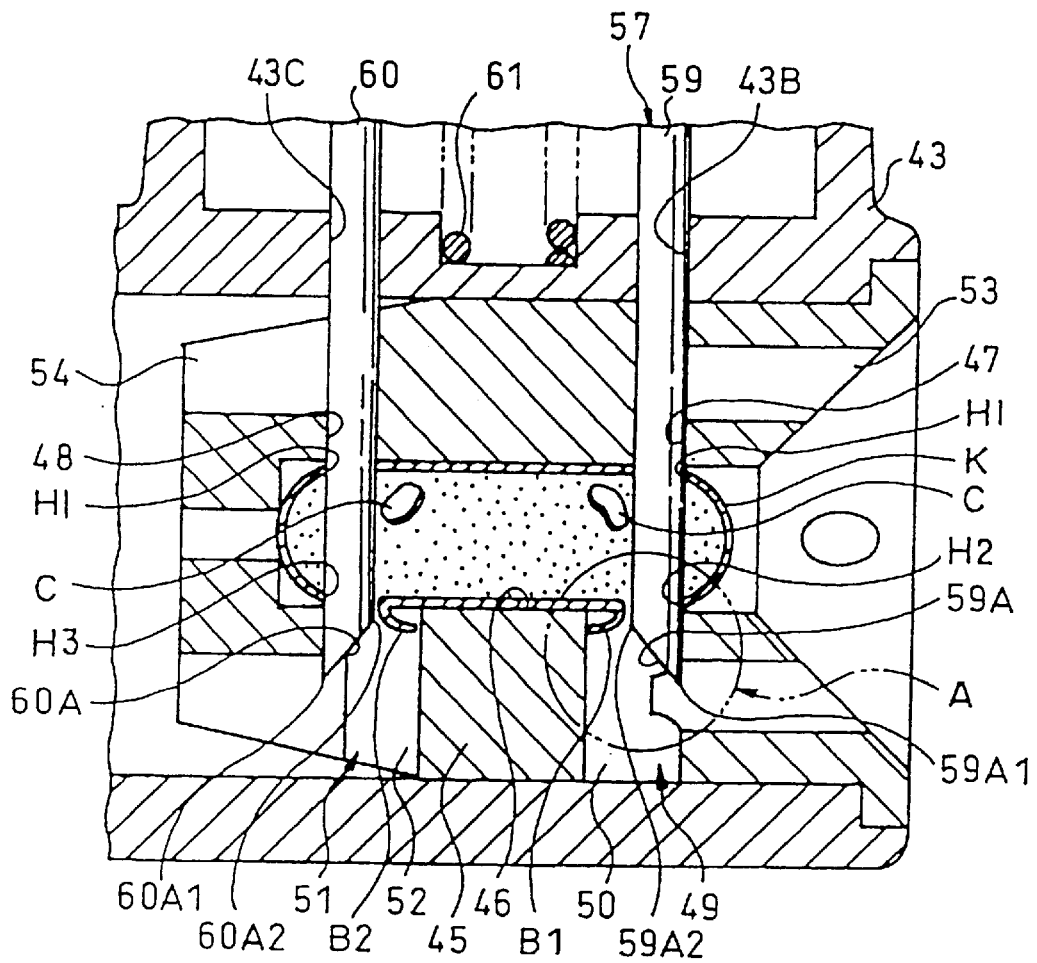
FIG. 18 is a fragmentary sectional view of an essential part, showing a state where the capsule accommodated in the capsule holder is perforated by the perforating tool.

46 designates a capsule accommodating hole which is located at the central portion of the capsule holder 45 and formed extending axially. The one end side of the capsule accommodating hole 45 is opened to the inflow-side depression 45A. The capsule K is fitted in the capsule accommodating hole 46 from the inflow-side depression 45A as shown in FIG. 18. Here, the capsule K is formed into the shape of an elongate cylinder, in which the inside of the capsule K is filled with granular medicine.

47 designates an inflow-side pin insertion hole which is located at the side of the perforating tool 57 and formed radially in the capsule holder 45 so as to be in communication with the capsule accommodating hole 46 at a position near the one side. The pin insertion hole 47 is disposed coaxial and aligned with the pin hole 43B of the holder accommodating section 43.

Additionally, 48 designates an outflow-side pin insertion hole which is located at the side of the perforating tool 57 and formed axially separate from the pin insertion hole 47. The outflow-side pin insertion hole 48 is formed extending radially in the capsule holder 45 so as to be in communication with the capsule accommodating hole 46 at a position near the other side. The pin insertion hole 48 is disposed coaxial and aligned with the pin hole 43C of the holder accommodating section 43.

Figure 17:
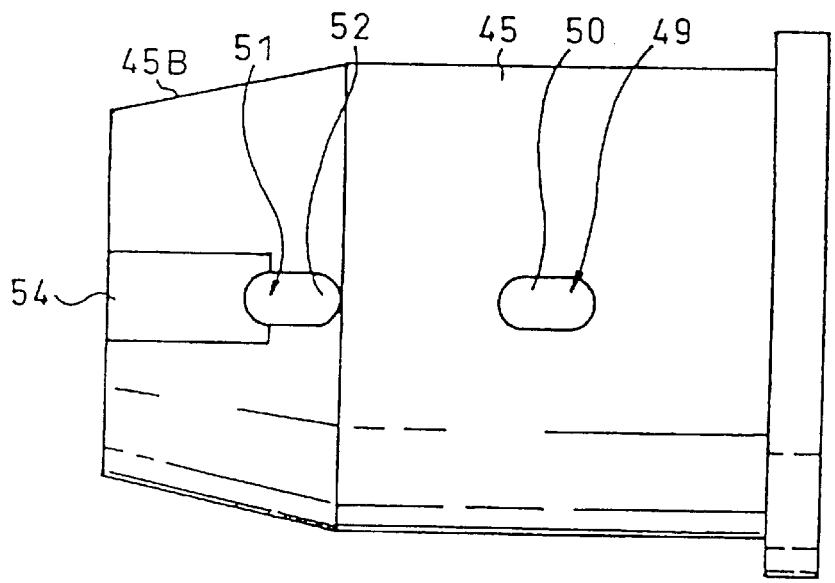
FIG. 17 is an external appearance view of the capsule holder as viewed in the direction of arrows III—III of FIG. 16.

49 designates an inflow-side pin insertion hole which is located at an opposite side of the capsule accommodating hole 46 with respect to the perforating tool 57 and formed extending radially in the capsule holder 45 so as to be in communication with the capsule accommodating hole 46 at a position near the one side. As shown in FIG. 17, the pin insertion hole 49 is located at one side of the capsule holder 45 and has an arcuate cross-section which is coaxial with the pin insertion hole 47. The pin insertion hole 49 is formed as an elongate hole which elongates in the axial direction of the capsule accommodating hole 46. Additionally, the pin insertion hole 49 includes a burr releasing space 50 which is located at the other side or the side of the rear end portion 59A2 of the an inclined face 51A formed at the tip end side of a pin 59 which will be discussed after.

Figure 19:
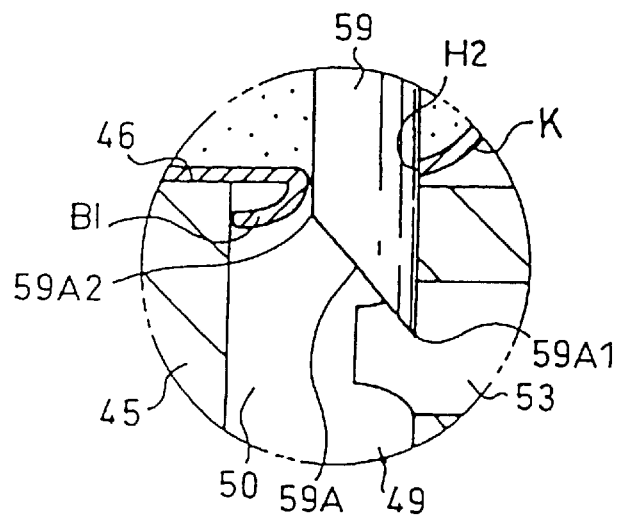
FIG. 19 is an enlarged sectional view of an essential part, showing a section indicated by an arrow A in FIG. 18.

Here, as shown in FIGS. 18 and 19, the above-mentioned burr releasing space 50 is adapted to allow a burr B1 (which will be discussed after) to be bent in a state where the burr B1 is left integral with the capsule K, when a hole H2 in communication with the pin insertion hole 49 is formed in the capsule K by the pin 59.

51 designates an outflow-side pin insertion hole which is located at an opposite side of the capsule accommodating hole 46 with respect to the perforating tool 57. The outflow-side pin insertion hole 51 is formed axially separate from the pin insertion hole 49 and formed extending radially in the capsule holder 45 so as to be in communication with the capsule accommodating hole 46 at a position near the other side. The pin insertion hole 51 is located at the other side of the capsule holder 45 and has an arcuate cross-section which is coaxial with the pin insertion hole 48. The pin insertion hole 51 is formed as an elongate hole which elongates in the axial direction of the capsule accommodating hole 46. Additionally, the pin insertion hole 51 includes a burr releasing space 52 which is located at one side or the side of the rear end portion 60A2 of the an inclined face 60A formed at the tip end side of a pin 60 which will be discussed after.

Here, the above-mentioned burr releasing space 52 is adapted to allow a burr B2 (which will be discussed after) to be bent in a state where the burr B2 is left integral with the capsule K, when a hole H3 in communication with the pin insertion hole 49 is formed in the capsule K by the pin 60, similarly to the burr releasing space 50 formed in the above-mentioned inflow-side pin insertion hole 49.

53, 53 designate respectively inflow-side passages serving as inflow-side air flow passages which are located radially outward relative to the capsule accommodating hole 46 and formed at one side of the capsule holder 45. Each inflow-side passage 53 is formed extending axially in a manner that its one end side is opened to the inflow-side depression 45A while the other end side is in communication with the pin insertion hole 47, 49. By this, each inflow-side passage 53 is communicated with the capsule accommodating hole 46 through the pin insertion hole 47, 49.

54, 54 designate respectively outflow-side passages serving as outflow-side air flow passages which are located radially outward relative to the capsule accommodating hole 46 and formed at the other side of the capsule holder 45. Each outflow-side passage 54 is formed into the groove shape by cutting out the outflow-side tapered surface 45B in a manner that its one end side is in communication with the outflow-side pin insertion hole 48, 51 while the other end side is opened to the other end face of the capsule holder 45. Each outflow-side passage 54 is communicated with the capsule accommodating hole 46 through the pin insertion hole 48, 51.

55, 55 designate respectively two auxiliary air flow passages (shown only one of them) which are formed respectively at positions which shift an angle of 90 degrees relative to the pin insertion holes 47, 48, 48, 51. The two auxiliary air flow passages 55, 55 are formed to pierce axially the capsule holder 45. Each auxiliary air passage 55 functions to cancel difficulty in breathing during the patient's breathing-in by increasing a flow amount of air flowing when the patient breathes in.

46 designates a small diameter hole which is formed at the central portion on the other end of the capsule holder 45 in a manner to be in communication with the capsule accommodating hole 46. The small diameter hole 56 is used for removing the capsule K left in the capsule accommodating hole 46 after medicine is administered to the patient, by using a jig (not shown).

57 designates a perforating tool for forming holes H1, H1, H2, H3 (which will be discussed after) in the capsule K accommodated in the capsule accommodating hole 46. The perforating tool 57 generally includes a supporting section 58 which is movably supported within the guide cylindrical section 43A, pins 59, 60 each of which has a tip end side located in the pin hole 43B, 43C and a base end side fixed to the supporting section 58, and a return spring 61 disposed between the above-mentioned supporting section 58 and the holder accommodating section 43. The return spring 61 functions to bias the supporting section 58 in such a direction that the pin 59, 60 separates from the capsule K, so as to return the pins 59, 60 to their initial position after perforation of the capsule K.

Here, the above-mentioned pin 59 is formed at its tip end side with an inclined face 59A whose tip end section 59A1 has an acute angle in section, in which the diametrically opposite side of the inclined face 59A relative to the tip end section 59A1 is a rear end section 59A2. Additionally, the pin 59 is installed to the supporting section in such a manner that the tip end section 59A1 is located at one side while the rear end section 59A2 is located at the other side. The pin 59 pierces the capsule K to form the hole H1 by plunging the tip end section 59A1 of the inclined face 59A into the capsule K. Additionally, the burr B1 of the capsule K is bent to enter the burr releasing space 50 formed at the other side of the pin insertion hole 49 by the inclined face 59 thereby forming the hole H2.

Additionally, the above-mentioned pin 60 is formed at its tip end side with an inclined face 60A which has a tip end section 60A1 having an acute angle in section, in which the diametrically opposite side relative to the tip end section 60A1 is a rear end section 60A2, generally similarly to the above-mentioned pin 59. However, the pin 60 is different from the pin 59 in a point that the pin 60 is installed to the supporting section 58 in a manner that the tin end section 60A1 of the inclined face 60A is located at the other side while the rear end section 60A2 is located at one side. The pin 60 pierces the capsule K to form the hole H1, and the burr B2 is bent to enter the burr releasing space 52 by the inclined face 60A thereby to form the hole H3.

Thus, the perforating tool 57 operates as follows: The supporting section 58 is thrust into the guide cylindrical section 43A against the bias of the return spring 61 so that the respective pins 59, 60 are inserted into the pin insertion holes 47, 48 and the likes. Consequently, the inclined faces 59A, 60A at the tip end sides of the pins 59, 60 pierce the capsule K in the capsule accommodating hole 46, so that the diametrically piercing holes H1, H1, H2, H3 are formed in the capsule K. Additionally, when a pushing force against the supporting section 58 is removed, the supporting section 58 and the respective pins 59, 60 return back to their initial position.

The inhaling type medicine administering device according to this embodiment has an arrangement as discussed above. Next, discussion will be made on a preparation operation made before the patient inhales medicine and on flow of air and medicine during inhalation of medicine.

First, the capsule K is fitted into the capsule accommodating hole 46 from the one end of the capsule accommodating hole 46. Since the one end face of the capsule holder 45 is the tapered inflow-side depression 45A, the capsule K can be readily guided into the capsule accommodating hole 46.

Subsequently, the supporting section 58 of the perforating tool 57 is pushed in along the guide cylindrical section 43A under a condition where the capsule K has been accommodated within the capsule accommodating hole 46. By this, the respective pins 59, 60 are inserted along the insertion holes 47, 48; 49, 51, so that the respective pins 59, 60 pierce the capsule K accommodated in the capsule accommodating hole 46.

Here, perforation for the capsule K will be discussed. When the pin 59 pierces the capsule K, first the hole H1 in communication with the pin insertion hole 4 is formed in the capsule. This hole H1 is formed piercing the capsule K, in which capsule pieces C are stored in the capsule K.

Subsequently, the hole H2 in communication with the pin insertion hole 49 is formed. At this time, the pin insertion hole 49 has the burr releasing space 50 which extends to the side of the suction mouth 44, and the pin 59 is formed at its tip end side with the inclined face 59A which inclines at the side of the suction mouth 4. Consequently, when the tip end section 59A1 of the inclined face 59A is plunged into the capsule K, the burr B1 of the capsule K is bent under the action of the inclined face 59A and installed in the burr releasing space 50. By this, the hole H2 can be formed in the capsule K without separation of the burr B1 from capsule K.

Additionally, when the pin 60 pierces the capsule K, first the hole H1 in communication with the pin insertion hole 48 is formed in the capsule K. This hole H1 is formed piercing the capsule K, in which the capsule pieces C are stored in the capsule K.

Subsequently, the hole H3 in communication with the pin insertion hole 51 is formed. At this time, the pin insertion hole 51 has the burr releasing space 52, and the inclined face 60A is formed at the tip end side of the pin 60. Consequently, when the tip end section 60A1 of the inclined face 60A is plunged into the capsule K, burr B2 of the capsule K is bent toward the one side by the inclined face 60A and installed in the burr releasing space 52. By this, the hole H3 is formed in the capsule K without separation of the burr B2 from the capsule K.

After the four holes H1, H1, H2, H3 have been formed in the capsule K, the supporting section 58 and the respective pins 59, 60 are returned to their initial position.

Figure 20:
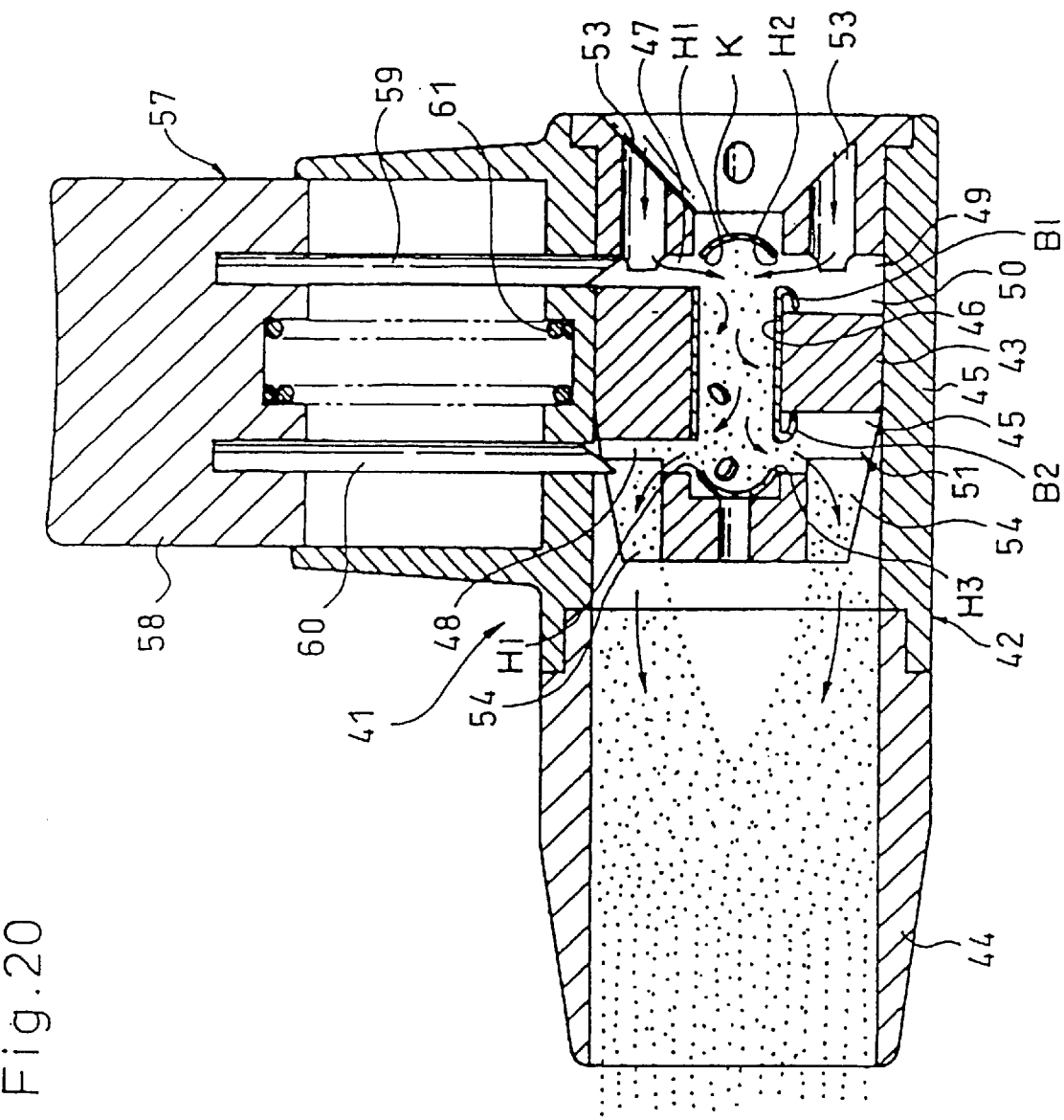
FIG. 20 is a cross-sectional view showing the inhaling type medicine administering device in a state where medicine within the capsule is inhaled.

Next, discussion will be made on flow of air and medicine within the inhaling type medicine administering device at the time when the patient inhales medicine, with reference to FIG. 20.

First, the patient holds the other end side of the suction mouth 44 in his or her mouth, and breathes in under this condition. By this, as indicated by arrows in FIG. 20, air flows from each inflow-side passage 53 through the inflow-side pin insertion holes 47, 49 to the side of the capsule accommodating hole 45, and flows into the capsule K through the holes H1, H2 at the one side of the capsule K. Air flown into the capsule K compulsorily spreads granular medicine filled in the capsule K so as to mix medicine into air.

Air which thus contains medicine in the capsule K is released from the holes H1, H3 at the other side of the capsule K to the side of the suction mouth 44 through the outflow-side pin insertion holes 48, 51 and each outflow-side passage 54, and then sucked into the lungs of the patient from the suction mouth 44 through the inside of the mouth and the trachea of the patient. Thus, medicine can be administered into the lungs of the patient.

Additionally, during the above-mentioned inhalation of medicine, each capsule piece C produced upon formation of the hole H1 is stored in the capsule K, and the burrs B1, B2 produced upon formation of the holes H2, H3 are left integral with the capsule K. As a result, it can be prevented that the broken pieces and the like of the capsule K separate from the capsule K so as to be left inside the capsule holder 45 and the like or sucked by the patient.

Accordingly, according to this embodiment, the pin insertion holes 49, 51 have the burr releasing spaces 50, 52, and therefore the holes H2, H3 are formed under a condition where the burrs B1, B2 produced upon perforation are left integral with the capsule K without being separated from the capsule K. Consequently, broken pieces of the capsule K can be prevented from entering each passage and the like as discussed in connection with the conventional technique. Accordingly, a cleaning operation for removing broken pieces of the capsule K can be simplified, while treatment of the inhaling type medicine administering device can be facilitated.

Besides, each capsule piece C separated from the capsule K upon formation of each hole H1 is stored in the capsule K, and the burrs B1, B2 are left integral with the capsule K. Therefore, the patient can be prevented from having a coughing fit upon sucking in the pieces together with medicine during inhalation of medicine, so that medicine can be effectively inhaled into his or her lungs thereby improving reliability to the inhaling type medicine administering device.

Furthermore, the pin insertion holes 49, 51 have the burr releasing spaces 50, 52, and therefore a clearance between the pin 59, 60 and the pin insertion hole 49, 51 is enlarged thereby lowering precision in assembly. This can lower a machining cost of each component part and lower production cost by improving an assembly operationability during production.

Figure 21:
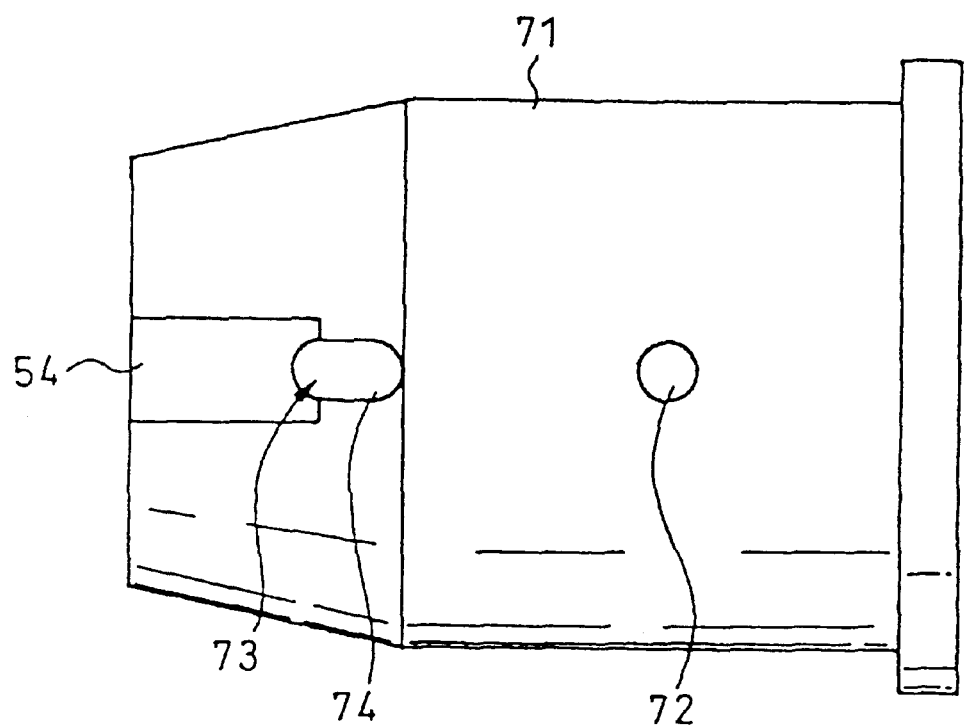
FIG. 21 is an external appearance view as viewed from the same position as that of FIG. 17, showing the capsule holder according to a fourth embodiment of the present invention.

Next, a fourth embodiment of the present invention will be discussed with reference to FIG. 21. This embodiment features to be arranged such that the burr releasing space is formed only in the pin insertion hole located at the suction mouth side. In this embodiment, the same reference numerals are assigned to the same component elements as those in the above-mentioned third embodiment, thereby omitting explanation thereof.

71 designates a capsule holder which is used in place of the capsule holder 45 in the third embodiment. 72 designates an inflow-side pin insertion hole which is formed in the capsule holder 71 located on an opposite side of the capsule accommodating hole 46 with respect to the perforating tool 57 and at one side of the capsule holder 71. The pin insertion hole 72 is formed as an annular hole similarly to the pin insertion holes 47, 48 located on the side of the perforating tool 57.

Additionally, a pin insertion hole 73 of the elongate hole shape is formed at the side of the suction mouth 44 of the capsule holder 71. The pin insertion hole 73 includes a burr releasing space 74.

Accordingly, also in the thus arranged fourth embodiment, the generally same functions and effects as those in the above-mentioned third embodiment can be obtained. In this embodiment, during perforation, broken pieces of the capsule K enter the pin insertion hole 72; however, these broken pieces can be stored in the capsule K under the influence of air generated during sucking of medicine.

Figure 22:
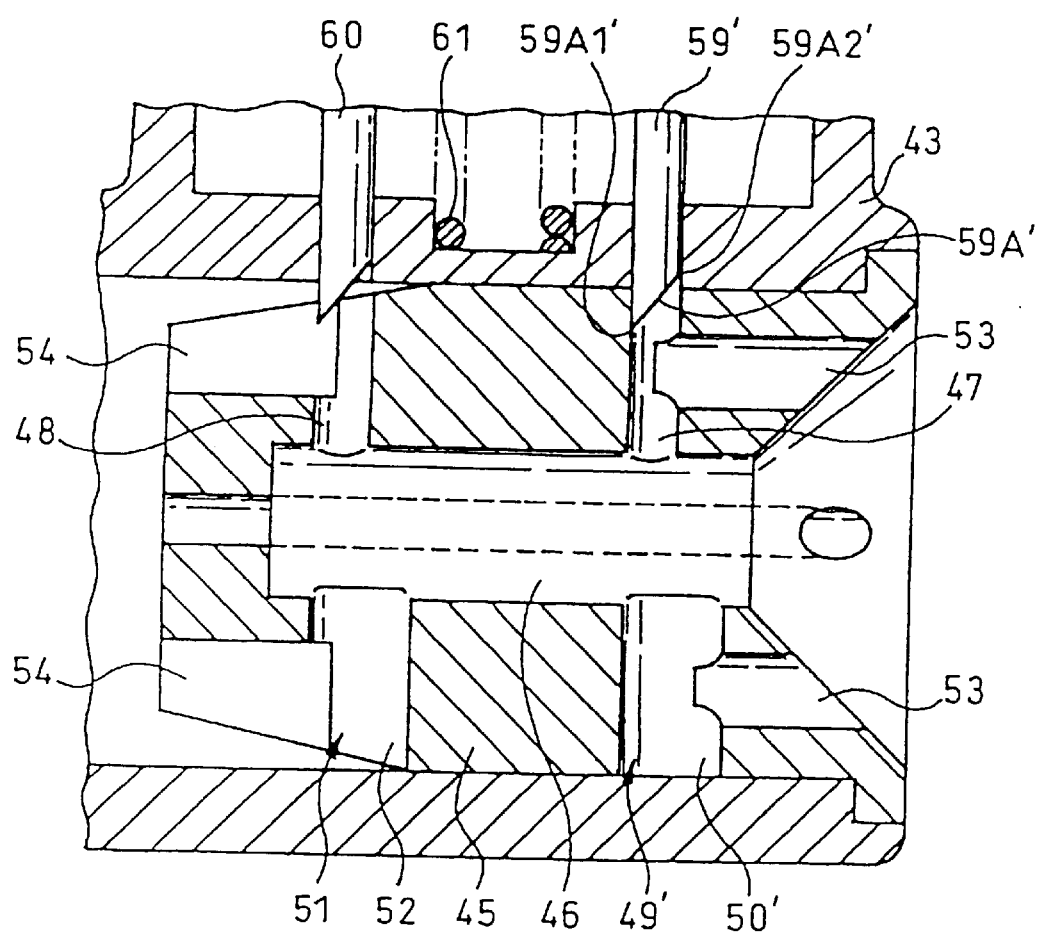
FIG. 22 is an enlarged fragmentary sectional view of an essential part, showing the holder accommodating section, the capsule holder, the pins of the perforating tool and the like according to a first modified example of the present invention.
Figure 23:
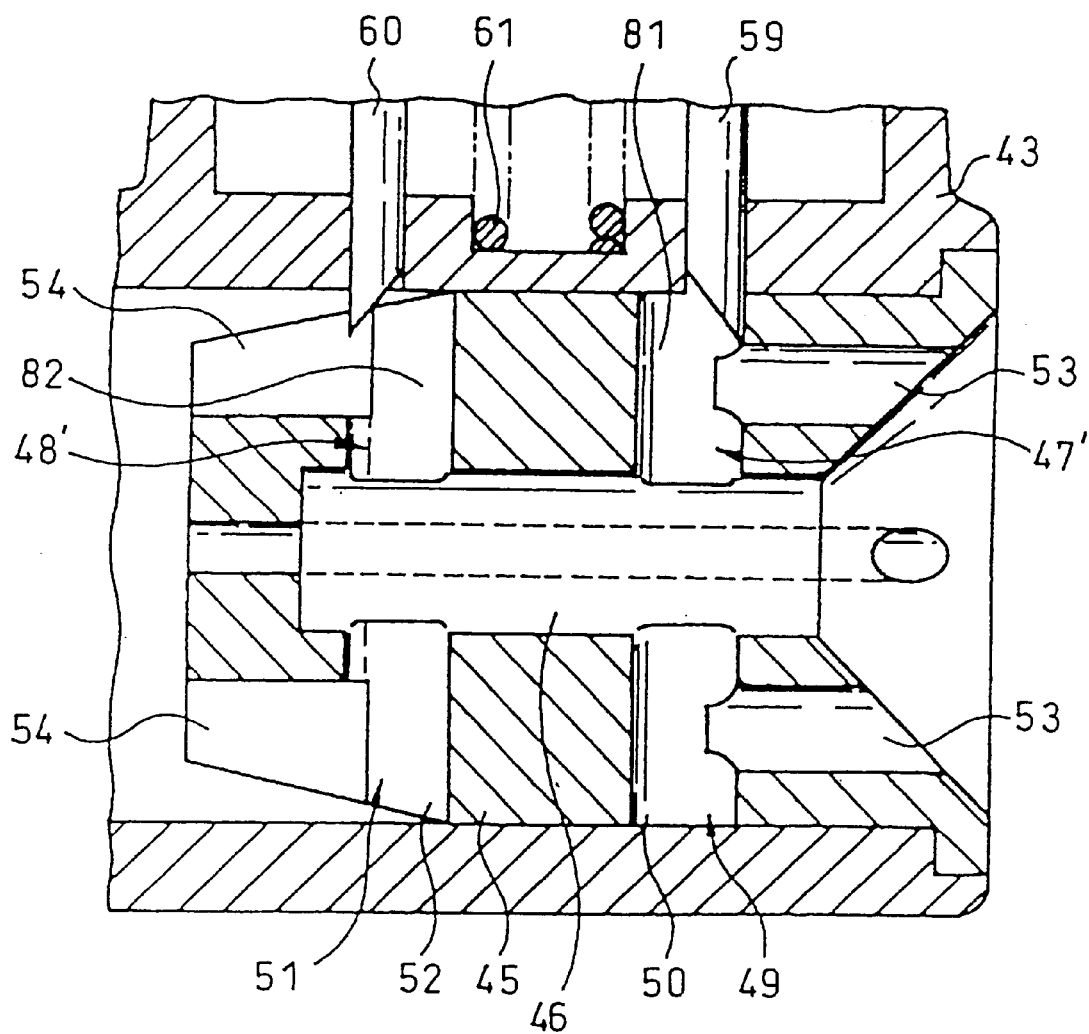
FIG. 23 is an enlarged fragmentary sectional view of an essential part, showing the holder accommodating section, the capsule holder, the pins of the perforating tool and the like according to a second modified example.

While the above-mentioned respective embodiments have been discussed using examples in which the tip end section 59A1 of the inclined face 59A formed in the pin 59 is located at one side while the rear end section 59A2 is located at the other side; and the tip end section 60A1 of the inclined face 60A formed at the tip end side of the pin 60 is located at the other side while the rear end section 60A2 is located at the one side, the present invention is not limited to this, in which, for example, the tip end section 59A1' of the inclined face 59A' formed in the pin 59' may be located at the one side while the rear end section 59A2' may be located at the other side, like in a first modified example shown in FIG. 22. In this case, the burr releasing space 50' may be formed to be located at one side of the pin insertion hole 49'.

Additionally, although the above-mentioned first embodiment is arranged such that the burr releasing spaces 10, 12 are respectively formed in the pin insertion holes 9, 11 which are located on an opposite side of the capsule accommodating hole 6 with respect to the perforating tool 17, this may be replaced with an arrangement which is, for example, like that in a second modified example shown FIG. 9 in which the burr releasing spaces 41, 42 are respectively formed in the pin insertion holes 7', 8' which are located at the side of the perforating tool 17. In this case, erroneous assembly of the capsule holder 5 to the holder accommodating section 3 can be prevented. Additionally, this principle can be applied to the second embodiment and the first modified example.

Furthermore, while the above-mentioned respective embodiments are arranged such that the pin insertion holes 9, 11 having the burr releasing spaces 10, 12 are formed as the elongate holes, this invention is not limited to this, and therefore each pin insertion hole may be, for example, circular, oval, and rectangular as far as burr can be allowed to be bent during perforation.

INDUSTRIAL USABILITY

As discussed above, the inhaling type medicine administering device according to the present invention can be extensively applied to ones in which fine granules and the like filled in a capsule are inhaled upon breaking the capsule.

What is claimed is:

1. An inhaling type medicine administering device comprising:
    a medicine administering device main body including a holder accommodating section located at an axial one side of said main body, and a suction mouth located at an axial other side of said main body;
    a capsule holder movably disposed in said holder accommodating section to be able to move axially in and out of said holder accommodating section, said capsule holder having a depression therein that forms a capsule holding space with said holder accommodating section of said medicine administering device main body;
    an air flow passage having an inflow-side for establishing communication between said capsule holding space and atmospheric air, and an outflow-side for establishing communication between said capsule holding space and said suction mouth in order to supply medicine within a capsule held in said capsule holding space to said suction mouth; and
    a perforating tool disposed in said medicine administering device main body in order to form a hole in the capsule held in said capsule holding space, said hole being in communication with said air flow passage.

2. An inhaling type medicine administering device as claimed in claim 1, wherein said air flow passage includes an inflow-side air flow passage which is located at the axial one side of said capsule holder so as to be in communication with said capsule holding space; and an outflow-side air flow passage which is located at the axial other side of said capsule holder so as to be in communication with said capsule holding space.

3. An inhaling type medicine administering device as claimed in claim 1, wherein said holder accommodating section has a capsule fitting groove, said capsule fitting groove of said holder accommodating section and said depression of said capsule holder together forming said capsule holding space.

4. An inhaling type medicine administering device as claimed in claim 1, wherein said capsule holder includes a reverse-flow preventing valve adapted to allow air through said air flow passage toward said suction mouth and to prevent air from flowing in a reverse direction.

5. An inhaling type medicine administering device as claimed in claim 1, wherein said capsule holder includes a grasping section for getting said capsule holder in and out of said holder accommodating section.

6. An inhaling type medicine administering device as claimed in claim 1, further comprising a locating engagement section formed between said holder accommodating section of said medicine administering device main body and said capsule holder, said locating engagement section being adapted to locate said capsule holder at a pushed-in position where said capsule holder is pushed in said holder accommodating section or at a drawn-out position where said capsule holder is drawn out of said holder accommodating section.

7. An inhaling type medicine administering device as claimed in claim 1, characterized in that said capsule holder is formed with pin insertion holes in which pins of said perforating tool pierce, wherein at least said pin insertion hole located at the side of said suction mouth has a burr releasing space which allows burr to be bent, said burr being produced upon perforation when a hole is formed in the capsule.

8. An inhaling type medicine administering device as claimed in claim 7, characterized in that each pin of said perforating tool has a tip end section which is formed as an inclined face having an acute angle in section, wherein said burr releasing space is formed at the rear end side of the inclined face of said pin so as to connect with said pin insertion hole.

9. An inhaling type medicine administering device as claimed in claim 7, wherein said pin insertion hole is formed as an elongate hole.

10. An inhaling type medicine administering device comprising:

- a medicine administering device main body having a capsule accommodating hole located at an axial one side of said main body, and a suction mouth located at an axial other side of said main body;
- pin insertion holes formed separate from each other in an axial direction of said capsule accommodating hole and formed piercing radially in said medicine administering device main body so as to be in communication with said capsule accommodating hole;
- inflow-side and outflow-side air flow passages located radially outward of said capsule accommodating hole and formed piercing in an axial direction of said medicine administering device main body so that said air flow passages are respectively in communication with said pin insertion holes; and
- a perforating tool having pins that are respectively to be inserted through said pin insertion holes toward the capsule in order to form holes in said capsule in a state to be fitted in said capsule accommodating hole;
- wherein a burr releasing space is formed in at least said pin insertion hole that is located on an opposite side of said capsule accommodating hole with respect to said perforating tool, of said respective pin insertion holes, said burr releasing space being adapted to allow burr produced upon perforation during perforation of the capsule to be bent.

11. An inhaling type medicine administering device as claimed in claim 10, wherein said burr releasing space is formed only in said pin insertion hole located at said side of the suction mouth of said respective pin insertion holes.

12. An inhaling type medicine administering device as claimed in claim 10, wherein each pin of said perforating tool has a tip end section which is formed as an inclined face having an acute angle in section, wherein said burr releasing space is formed at the rear end side of the inclined face of said pin so as to connect with said pin insertion hole.

13. An inhaling type medicine administering device as claimed in claim 10, wherein said pin insertion hole is formed as an elongate hole.

* * * * *